US007008897B2

(12) United States Patent
Takaoki

(10) Patent No.: US 7,008,897 B2
(45) Date of Patent: Mar. 7, 2006

(54) METAL COMPOUND, AND CATALYST COMPONENT AND CATALYST FOR ADDITION POLYMERIZATION, AND PROCESS FOR PRODUCING ADDITION POLYMER

(75) Inventor: Kazuo Takaoki, Albany, CA (US)

(73) Assignee: Sumitomo Chemical Company, Limited, Osaka (JP)

( * ) Notice: Subject to any disclaimer, the term of this patent is extended or adjusted under 35 U.S.C. 154(b) by 8 days.

(21) Appl. No.: 10/756,605

(22) Filed: Jan. 14, 2004

(65) Prior Publication Data

US 2004/0209763 A1  Oct. 21, 2004

(30) Foreign Application Priority Data

Jan. 20, 2003  (JP) .............................. 2003-011085

(51) Int. Cl.
*B01J 31/00* (2006.01)
*B01J 37/00* (2006.01)
*C08F 4/02* (2006.01)
*C08F 4/60* (2006.01)

(52) U.S. Cl. .................. 502/103; 502/150; 502/153; 502/154; 502/156; 502/162; 526/72

(58) Field of Classification Search ................ 502/103, 502/150, 153, 154, 156, 162; 526/72
See application file for complete search history.

(56) References Cited

U.S. PATENT DOCUMENTS 4,542,199 A  9/1985  Kaminsky et al.

| 5,153,157 A | 10/1992 | Hlatky et al. |
| 5,621,126 A | 4/1997 | Canich et al. |
| 5,942,568 A * | 8/1999 | Niino et al. ................ 524/405 |
| 6,174,974 B1 * | 1/2001 | Starzewski et al. ......... 526/161 |
| 6,191,241 B1 * | 2/2001 | Starzewski et al. ......... 526/161 |
| 6,586,356 B1 | 7/2003 | Takaoki et al. |

OTHER PUBLICATIONS

K. Whitmire et al., "Oligomerization and Oxide Formation in Bismuth Aryl Alkoxides: Synthesis and Characterization of $Bi_4(\mu_4-O)(\mu-OC_6F_5)_6$ $(\mu_3-OBi(\mu-OC_6F_5)_3)_2(C_6H_5CH_3)$, $Bi_8(\mu_4-O)_2(\mu_3-O)_2(\mu-OC_6F_5)_{16}Bi_6(\mu_3-O)_4(\mu_3-OC_6F_5)(\mu_3-OBi(OC_6F_5)_4)_3$, $NaBi_4(\mu_3-O)_2(OC_6F_5)_9(THF)_2$, and $Na_2Bi_4(\mu_3-OC_6F_5)_{10}(THF)_2$", Inorg. Chem. 2000, 39, pp. 85-97.

C. Jones et al., "Hypervalent Bismuth Alkoxide Dimer Complexes: Synthesis, Structure, and Thermal Decompositions of $[Bi(OCH(CF_3)_2)_2(\mu-OCH(CF_3)_2)(THF)]_2$ and $[Bi(OC_6F_5)_2(\mu-OC_6F_5)X_a]_2$ $zY$ (X =Y $C_7H_8$, n =1, z =1 or 2: X =THF, Y =$C_6H_{14}$, n =2, z =0 or 1)", Inorg. Chem. 1993, 32, pp. 5136-5144.

* cited by examiner

Primary Examiner—J. A. Lorengo
Assistant Examiner—Jennine Brown
(74) Attorney, Agent, or Firm—Sughrue Mion, PLLC

(57) ABSTRACT

A metal compound obtained by a process comprising the step of contacting, in a specific ratio, a compound represented by the formula $BiL^1_r$, a compound represented by the formula $R^1_{s-1}TH$, and a compound represented by the formula $R^2_{3-n}J(OH)_n$; a catalyst component for addition polymerization comprising the metal compound; a catalyst for addition polymerization using the catalyst component; and a process for producing an addition polymer using the catalyst.

7 Claims, No Drawings

METAL COMPOUND, AND CATALYST COMPONENT AND CATALYST FOR ADDITION POLYMERIZATION, AND PROCESS FOR PRODUCING ADDITION POLYMER

FIELD OF THE INVENTION

The present invention relates to a metal compound; a catalyst component for addition polymerization comprising the metal compound; a catalyst for addition polymerization using the catalyst component for addition polymerization; and a process for producing an addition polymer.

BACKGROUND OF THE INVENTION

Since olefin polymers such as polypropylene and polyethylene are excellent in mechanical properties and chemical resistance, and excellent in balance between those properties and economical efficiency, they have been widely used in various fields such as a packaging field. These olef in polymers have conventionally been produced by polymerizing an olefin using a conventional type solid catalyst (multi-site catalyst), which combines a solid catalyst component obtained by using a metal compound of the Group IV such as titanium trichloride or titanium tetrachloride, with a metal compound of the Group 13 represented by an organoaluminum compound.

However, as a catalyst providing addition polymers having less stickiness and more excellent strength than those produced by the conventional catalyst, a so-called single site catalyst prepared by combining a catalyst component such as a metallocene complex or half metallocene complex with a co-catalyst component for activation such as an aluminoxane, and tri(n-butyl)ammonium tetrakis(pentafluorophenyl) borate, was proposed and with respect to the single site catalyst, improvements for using it in an industrial scale have been studied (e.g. U.S. Pat. Nos. 4,542,199, 5,621,126, 5,153,157).

Further, recently, a compound prepared by contacting diethylzinc and pentafluorophenol has been developed as a co-catalyst component for activation, and a catalyst prepared by contacting said co-catalyst component with the metallocene complex has been proposed as a high activity catalyst (e.g. U.S. Pat. No. 6,586,356).

However, according to the inventor's studies, when an olefin is addition-polymerized with the above-mentioned catalyst, its polymerization activity is not completely satisfactory.

SUMMARY OF THE INVENTION

Under the above-situations, an object of the present invention is to provide a metal compound used as a catalyst component of a catalyst for addition polymerization having an excellent polymerization activity; a catalyst component for addition polymerization comprising the metal compound; a catalyst for addition polymerization using the catalyst component for addition polymerization; and a process for producing an addition polymer using the catalyst for addition polymerization.

Namely, the present invention is a metal compound obtained by a process comprising the step of contacting the following components (a) to (c), wherein the amount of the component (b) contacted is from 0.1 to 8 mol, and the amount of the component (c) contacted is from 0.6 to 8 mol, per 1 mol of the component (a), respectively:

(a) a compound represented by the following formula [1]

$$BiL^1_r \qquad [1],$$

(b) a compound represented by the following formula [2]

$$R^1_{s-1}TH \qquad [2], \text{ and}$$

(c) a compound represented by the following formula [3], $$R^2_{3-n}J(OH)_n \qquad [3],$$

wherein r is a valence of Bi; $L^1$ is a hydrogen atom, a halogen atom, a hydrocarbon group or a hydrocarbon oxy group, and when two or more $L^1$'s exist, they may be the same or different from one another; T is a non-metal atom of the Group 15 or 16 in the periodic table; s is a valence of T; $R^1$ is an electron-withdrawing group or an electron-withdrawing group-containing group, and when two or more $R^1$'s exist, they may be the same or different from one another; n is 2 or 3; J is an atom of the Group 13 in the periodic table; and $R^2$ is a hydrocarbon group, and when two or more $R^2$'s exist, they may be the same or different from one another.

Also, the present invention is a catalyst component for addition polymerization comprising the above-mentioned metal compound.

Further, the present invention is a catalyst for addition polymerization obtained by a process comprising the step of contacting the above-mentioned catalyst component for addition polymerization with a compound (B) of a metal selected from the group consisting of metals of the Groups 3 to 12 and lanthanide series, and optionally an organoaluminum compound (C).

Still further, the present invention is a process for producing an addition polymer comprising the step of polymerizing an addition polymerizable monomer in the presence of the above-mentioned catalyst for addition polymerization.

DETAILED DESCRIPTION OF THE INVENTION

In the above formula [1], r, a valence of Bi, is 3 or 5, and preferably 3.

Examples of the halogen atom of $L^1$ are a fluorine atom, a chlorine atom, a bromine atom and an iodine atom. The hydrocarbon group of $L^1$ is preferably an alkyl group, an aryl group or an aralkyl group. The hydrocarbon oxy group of $L^1$ is preferably an alkoxy group or an aryloxy group.

Examples of the above-mentioned alkyl group are a methyl group, an ethyl group, a n-propyl group, an isopropyl group, a n-butyl group, a sec-butyl group, a tert-butyl group, an isobutyl group, a n-pentyl group, a neopentyl group, a n-hexyl group, a n-octyl group, a n-decyl group, a n-dodecyl group, a n-pentadecyl group and a n-eicosyl group.

These alkyl groups may be substituted with a halogen atom such as a fluorine atom, a chlorine atom, a bromine atom and an iodine atom. Examples of the alkyl group substituted with the halogen atom are a fluoromethyl group, a difluoromethyl group, a trifluoromethyl group, a chloromethyl group, a dichloromethyl group, a trichloromethyl group, a bromomethyl group, a dibromomethyl group, a tribromomethyl group, an iodomethyl group, a diiodomethyl group, a triiodomethyl group, a fluoroethyl group, a difluoroethyl group, a trifluoroethyl group, a tetrafluoroethyl group, a pentafluoroethyl group, a chloroethyl group, a dichloroethyl group, a trichloroethyl group, a tetrachloroethyl group, a pentachloroethyl group, a bromoethyl group, a dibromoethyl group, a tribromoethyl group, a tetrabromoethyl group, a pentabromoethyl group, a perfluoropropyl group, a perfluorobutyl group, a perfluoropentyl group, a perfluorohexyl group, a perfluorooctyl group, a perfluorododecyl group, a perfluoropentadecyl group, a perfluoroeicosyl group, a perchloropropyl group, a perchlorobutyl group, a perchloropentyl group, perchlorohexyl group, a perchlorooctyl group, a perchlorododecyl group, a perchloropentadecyl group, a perchloroeicosyl group, a perbromopropyl group, a perbromobutyl group, a perbromopentyl group, a perbromohexyl group, a perbromooctyl group, a perbromododecyl group, a perbromopentadecyl group and a perbromoeicosyl group.

The alkyl group as $L^1$ is preferably an alkyl group having 1 to 20 carbon atoms, and more preferably a methyl group, an ethyl group, an isopropyl group, a n-butyl group, a tert-butyl group or an isobutyl group.

Examples of the aryl group as $L^1$ are a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, an isobutylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group.

The aryl group is preferably an aryl group having 6 to 20 carbon atoms, and more preferably a phenyl group or a 2-, 3-, or 4-tolyl group.

Examples of the aralkyl group as $L^1$ are a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-timethylphenyl)methyl group, a (2,3,5-timethylphenyl)methyl group, a (2,3,6-timethylphenyl)methyl group, a (3,4,5-timethylphenyl)methyl group, a (2,4,6-timethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl)methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl)methyl group, a (n-octylphenyl)methyl group, a (n-decylphenyl)methyl group, a (tetradecylphenyl)methyl group, a naphthylmethyl group and an anthracenylmethyl group.

The aralkyl group as $L^1$ is preferably an aralkyl group having 7 to 20 carbon atoms, and more preferably a benzyl group.

Examples of the alkoxy group as $L^1$ are a methoxy group, an ethoxy group, a n-propoxy group, an isopropoxy group, a n-butoxy group, a sec-butoxy group, a tert-butoxy group, an isobutoxy group, a n-pentyloxy group, a neopentyloxy group, a tert-pentyloxygroup, a n-hexyloxygroup, a n-heptyloxygroup, a n-octyloxy group, a n-decyloxy group, a n-dodecyloxy group, a n-pentadecyloxy group and a n-eicosyl oxy group.

The alkoxy group as $L^1$ is preferably an alkoxy group having 1 to 20 carbon atoms, and more preferably a methoxy group, an ethoxy group, an isopropoxy group, a tert-butoxy group, an isobutoxy group, a neopentoxyl group or a tert-pentyloxy group.

Specific examples of the aryloxy group as $L^1$ are a phenoxy group, a 2-tolyloxy group, a 3-tolyloxy group, a 4-tolyloxy group, a 2,3-xylyloxy group, a 2,4-xylylphenoxy group, a 2,5-xylyloxy group, a 2,6-xylyloxy group, a 3,4-xylyloxy group, a 3,5-xylyloxy group, a 2,3,4-trimethylphenoxy group, a 2,3,5-trimethylphenoxy group, a 2,3,6-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, a 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, an isobutylphenoxy group, a n-pentylphenoxy group, a neopentylphenoxy group, a n-hexylphenoxy group, a n-octylphenoxy group, a n-decylphenoxy group, a n-tetradecylphenoxy group, a naphthoxy group and an anthrathenoxy group.

The aryloxy group is preferably an aryloxy group having 6 to 20 carbon atoms, and more preferably a phenoxy group.

These alkyl, aryl, aralkyl, alkoxy and aryloxy groups above-mentioned as $L^1$ may be respectively substituted with a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

As $L^1$ in the above formula [1], preferred is a halogen atom, an alkyl group, an aryl group, an alkoxy group or an aryloxy group, more preferred is a halogen atom, an aryl group, an alkoxy group or an aryloxy group, and particularly preferable is an aryl group.

Examples of the compound (a) represented by the formula [1] are a halogenated bismuth (III) such as bismuth (III) fluoride, bismuth (III) chloride, bismuth (III) bromide and bismuth (III) iodide; a trialkyl bismuth such as trimethyl bismuth; a triaryl bismuth such as triphenyl bismuth; a trialkoxy bismuth such as trimethoxy bismuth, triethoxy bismuth, triisoprpoxy bismuth, tri(tert-butoxy)bismuth, triisobutoxy bismuth, trineopentyloxy bismuth and tri(tert-pentyloxy)bismuth; a triaryloxy bismuth such as triphenoxy bismuth, tri(2-tolyloxy)bismuth, tri(3-tolyloxy)bismuth, tri(4-tolyloxy)bismuth, tri(2,3-xylyloxy)bismuth, tri(2,4-xylyloxy)bismuth, tri(2,5-xylyloxy)bismuth, tri(2,6-xylyloxy)bismuth, tri(3,4-xylyloxy)bismuth, tri(3,5-xylyloxy)bismuth, tri(2,3,4-trimethylphenoxy)bismuth, tri(2,3,5-trimethylphenoxy)bismuth, tri(2,3,6-trimethylphenoxy)bismuth, tri(2,4,6-trimethylphenoxy)bismuth, tri(3,4,5-trimethylphenoxy)bismuth, tri(2,3,4,5-tetramethylphenoxy)bismuth, tri(2,3,4,6-tetramethylphenoxy)bismuth, tri(2,3,5,6-tetramethylphenoxy)bismuth, tri(pentamethylphenoxy)bismuth, tri(ethylphenoxy)bismuth, tri(n-propylphenoxy)bismuth, tri(isopropylphenoxy)bismuth, tri(n-butylphenoxy)bismuth, tri(sec-butylphenoxy)bismuth, tri(tert-butylphenoxy)bismuth, tri(isobutylphenoxy)bismuth, tri(n-pentylphenoxy)bismuth, tri(neopentylphenoxy)bismuth, tri(n-hexylphenoxy)bismuth, tri(n-octylphenoxy)bismuth, tri(n-decylphenoxy)bismuth, tri(n-dodecylphenoxy)bismuth, tri(n-tetradecylethylphenoxy)bismuth, trinaphtyloxy bismuth and trianthracenyloxy bismuth; a halogenated bismuth(V) such as bismuth(V)fluoride, bismuth(V)chloride, bismuth(V)bromide and bismuth(V)iodide; a pentaalkyl bismuth such as pentamethyl bismuth; a pentaalkoxy bismuths such as pentamethoxy bismuth and pentaethoxy bismuth; and a pentaaryloxy bismuths such as pentaphenoxy bismuth.

Among these, the compound (a) is preferably a halogenated bismuth (III), a trialkyl bismuth, a triaryl bismuth, a trialkoxy bismuth, a triaryloxy bismuth, more preferably a halogenated bismuth (III), a triaryl bismuth, a trialkoxy bismuth and a triaryloxy bismuth, and particularly preferably a triaryl bismuth such as triphenyl bismuth.

Examples of the non-metal atom of T of the Group 15 are a nitrogen atom and a phosphorous atom, and examples of the non-metal atom of T of the Group 16 are an oxygen atom and a sulfur atom. T is preferably a nitrogen atom or an oxygen atom, and particularly preferably an oxygen atom.

In the above formula [2], when T is a non-metal atom of the Group 15, s is 3, and when T is a non-metal atom of the Group 16, s is 2.

In the formula [2], as an index of the electron-withdrawing property, the substituent constant σ of the Hammet's rule is known, and a functional group, in which the substituent constant σ of the Hammet's rule is positive, can be mentioned as an electron-withdrawing group.

Examples of the electron-withdrawing group are a fluorine atom, a chlorine atom, a bromine atom, an iodine atom, a cyano group, a nitro group, a carbonyl group, a sulfonyl group, and a phenyl group. Examples of a group containing an electron-withdrawing group are a halogenated hydrocarbon group such as a halogenated alkyl group and a halogenated aryl group; a cyanated hydrocarbon group such as a cyanated aryl group; a nitrated hydrocarbon group such as a nitrated aryl groups; a hydrocarbonoxy carbonyl group such as an alkoxycarbonyl group, an aralkyloxycarbonyl group and an aryloxycarbonyl group; and an acyloxy group.

Examples of the halogenated alkyl group as $R^1$ are a fluoromethyl group, a chloromethyl group, a bromomethyl group, an iodomethyl group, a difluoromethyl group, a dichloromethyl group, a dibromomethyl group, a diiodomethyl group, a trifluoromethyl group, a trichloromethyl group, a tribromomethyl group, a triiodomethyl group, a 2,2,2-trifluoroethyl group, a 2,2,2-trichloroethyl group, a 2,2,2-tribromoethyl group, a 2,2,2-triiodoethyl group, a 2,2,3,3,3-pentafluoropropyl group, a 2,2,3,3,3-pentachloropropyl group, a 2,2,3,3,3-pentabromopropyl group, a 2,2,3,3,3-pentaiodopropyl group, a 2,2,2-trifluoro-1-trifluoromethylethyl group, a 2,2,2-trichloro-1-trichloromethylethyl group, a 2,2,2-tribromo-1-tribromomethylethyl group, a 2,2,2-triiodo-1-triiodomethylethyl group, a 1,1-bis(trifluoromethyl)-2,2,2-trifluoroethyl group, a 1,1-bis(trichloromethyl)-2,2,2-trichloroethyl group, a 1,1-bis(tribromomethyl)-2,2,2-tribromoethyl group, and a 1,1-bis(triiodomethyl)-2,2,2-triiodoethyl group.

Examples of the halogenated aryl group as $R^1$ are aryl groups in which a hydrogen atom of an aromatic ring in the group is substituted with a halogen such as a 2-fluorophenyl group, a 3-fluorophenyl group, a 4-fluorophenyl group, a 2-chlorophenyl group, a 3-chlorophenyl group, a 4-chlorophenyl group, a 2-bromophenyl group, a 3-bromophenyl group, a 4-bromophenyl group, a 2-iodophenyl group, a 3-iodophenyl group, a 4-iodophenyl group, a 2,6-difluorophenyl group, a 3,5-difluorophenyl group, a 3,4,5-trifluorophenyl group, a 2,6-dichlorophenyl group, a 3,5-dichlorophenyl group, a 2,6-dibromophenyl group, a 3,5-dibromophenyl group, a 2,6-diiodophenyl group, a 3,5-diiodophenyl group, a 2,4,6-trifluorophenyl group, a 2,4,6-trichlorophenyl group, a 2,4,6-tribromophenyl group, a 2,4,6-triiodophenyl group, a pentafluorophenyl group, a pentachlorophenyl group, a pentabromophenyl group, and a pentaiodophenyl group.

Further, examples of the (halogenated alkyl)aryl group as $R^1$ are aryl groups substituted with a halogenated alkyl group such as a 2-(trifluoromethyl)phenyl group, a 3-(trifluoromethyl)phenyl group, a 4-(trifluoromethyl)phenyl group, a 2,6-bis(trifluoromethyl)phenyl group, a 3,5-bis(trifluoromethyl)phenyl group, and a 2,4,6-tris(trifluoromethyl)phenyl group.

Examples of the cyanated aryl group as $R^1$ are a 2-cyanophenyl group, a 3-cyanophenyl group and a 4-cyanophenyl group.

Examples of the nitrated aryl group as $R^1$ are a 2-nitrophenyl group, a 3-nitrophenyl group and a 4-nitrophenyl group.

Examples of the alkoxycarbonyl group as $R^1$ are a methoxycarbonyl group, an ethoxycarbonyl group, a n-propoxycarbonyl group, an isopropoxycarbonyl group and a trifluoromethoxycarbonyl group.

An example of the aralkyloxycarbonyl group as $R^1$ is a benzyloxycarbonyl group.

Examples of the aryloxycarbonyl group as $R^1$ are a phenoxycarbonyl group and a pentafluorophenoxycarbonyl group.

Examples of the acyloxycarbonyl group as $R^1$ are a methycarbonyloxy group and an ethylcarbonyloxy group.

$R^1$ is preferably a halogenated hydrocarbon group; more preferably a halogenated alkyl group or a halogenated aryl group; further preferably a fluoroalkyl group, a fluoroaryl group, a chloroalkyl group or a chloroaryl group; furthermore preferably a fluoroalkyl group or a fluoroaryl group; particularly preferably a fluoromethyl group, a difluoromethyl group, a trifluoromethyl group, a 2,2,2-trifluoroethyl group, a 2,2,3,3,3-pentafluoropropyl group, a 2,2,2-trifluoro-1-trifluoromethylethyl group, a 1,1-bis(trifluoromethyl)-2,2,2-trifluoroethyl group, a 2-fluorophenyl group, a 3-fluorophenyl group, a 4-fluorophenyl group, a 2,4-difluorophenyl group, a 2,6-difluorophenyl group, a 3,4-difluorophenyl group, a 3,5-difluorophenyl group, a 2,4,6-trifluorophenyl group, a 3,4,5-trifluorophenyl group, a 2,3,5,6-tetrafluorophenyl group, a pentafluorophenyl group, a 2,3,5,6-tetrafluoro-4-trifluoromethylphenyl group, a 2,3,5,6-tetrafluoro-4-pentafluorophenylphenyl group, a perfluoro-1-naphthyl group, or a perfluoro-2-naphthyl group; and most preferably a trifluoromethyl group, a 2,2,2-trifluoro-1-trifluoromethylethyl group, a 1,1-bis(trifluoromethyl)-2,2,2-trifluoroethyl group, a 3,5-difluorophenyl group, a 3,4,5-trifluorophenyl group, or a pentafluorophenyl group.

When the compound (b) represented by the above formula [2] is an amine, examples thereof are di(fluoromethyl)amine, di(chloromethyl)amine, di(bromomethyl)amine, di(iodomethyl)amine, bis(difluoromethyl)amine, bis(dichloromethyl)amine, bis(dibromomethyl)amine, bis(diiodomethyl)amine, bis(trifluoromethyl)amine, bis(trichloromethyl)amine, bis(tribromomethyl)amine, bis(triiodomethyl)amine, bis(2,2,2-trifluoroethyl)amine, bis(2,2,2-trichloroethyl)amine, bis(2,2,2-tribromoethyl)amine, bis(2,2,2-triiodoethyl)amine, bis(2,2,3,3,3-pentafluoropropyl)amine, bis(2,2,3,3,3-pentachloropropyl)amine, bis(2,2,3,3,3-pentabromopropyl)amine, bis(2,2,3,3,3-pentaiodopropyl)amine, bis(2,2,2-trifluoro-1-trifluoromethylethyl)amine, bis(2,2,2-trichloro-1-trichloromethylethyl)amine, bis(2,2,2-tribromo-1-tribromomethylethyl)amine, bis(2,2,2-triiodo-1-triiodomethylethyl)amine, bis(1,1-bis(trifluoromethyl)-2,2,2-trifluoroethyl)amine, bis(1,1-bis(trichloromethyl)-2,2,2-trichloroethyl)amine, bis(1,1-bis(tribromomethyl)-2,2,2- tribromoethyl)amine, bis(1,1-bis(triiodomethyl)-2,2,2-triiodoethyl)amine, bis(2-fluorophenyl)amine, bis(3-fluorophenyl)amine, bis(4-fluorophenyl)amine, bis(2-chlorophenyl)amine, bis(3-chlorophenyl)amine, bis(4-chlorophenyl)amine, bis(2-bromophenyl)amine, bis(3-bromophenyl)amine, bis(4-bromophenyl)amine, bis(2-iodophenyl)amine, bis(3-iodophenyl)amine, bis(4-iodophenyl)amine, bis(2,6-difluorophenyl)amine, bis(3,5-difluorophenyl)amine, bis(2,6-dichlorophenyl)amine, bis(3,5-dichlorophenyl)amine, bis(2,6-dibromophenyl)amine, bis(3,5-dibromophenyl)amine, bis(2,6-diiodophenyl)amine, bis(3,5-diiodophenyl)amine, bis(2,4,6-trifluorophenyl)amine, bis(2,4,6-trichlorophenyl)amine, bis(2,4,6-tribromophenyl)amine, bis(2,4,6-triiodophenyl)amine, bis(pentafluorophenyl)amine, bis(pentachlorophenyl)amine, bis(pentabromophenyl)amine, bis(pentaiodophenyl)amine, bis(2-(trifluoromethyl)phenyl)amine, bis(3-(trifluoromethyl)phenyl)amine, bis(4-(trifluoromethyl)phenyl)amine, bis(2,6-di(trifluoromethyl)phenyl)amine, bis(3,5-di(trifluoromethyl)phenyl)amine, bis(2,4,6-tri(trifluoromethyl)phenyl)amine, bis(2-cyanophenyl)amine, bis(3-cyanophenyl)amine, bis(4-cyanophenyl)amine, bis(2-nitrophenyl)amine, bis(3-nitrophenyl)amine and bis(4-nitrophenyl)amine.

When the compound (b) is a phosphine, examples thereof are phosphine compounds in which a nitrogen atom is replaced with a phosphorus atom in the above-mentioned amine compounds.

When the compound (b) is an alcohol, examples thereof are fluoromethanol, chloromethanol, bromomethanol, iodomethanol, difluoromethanol, dichloromethanol, dibromomethanol, diiodomethanol, trifluoromethanol, trichloromethanol, tribromomethanol, triiodomethanol, 2,2,2-trifluoroethanol, 2,2,2-trichloroethanol, 2,2,2-tribromoethanol, 2,2,2-triiodoethanol, 2,2,3,3,3-pentafluoropropanol, 2,2,3,3,3-pentachloropropanol, 2,2,3,3,3-pentabromopropanol, 2,2,3,3,3-pentaiodopropanol, 2,2,2-trifluoro-1-trifluoromethylethanol, 2,2,2-trichloro-1-trichloromethylethanol, 2,2,2-tribromo-1-tribromomethylethanol, 2,2,2-triiodo-1-triiodomethylethanol, 1,1-bis(trifluoromethyl)-2,2,2-trifluoroethanol, 1,1-bis(trichloromethyl)-2,2,2-trichloroethanol, 1,1-bis(tribromomethyl)-2,2,2-tribromoethanol and 1,1-bis(triiodomethyl)-2,2,2-triiodoethanol.

When the compound (b) is a thiol compound, examples thereof are thiol compounds in which an oxygen atom is replaced with a sulfur atom in the above-mentioned alcohol compounds.

When the compound (b) is a phenol, examples thereof are 2-fluorophenol, 3-fluorophenol, 4-fluorophenol, 2-chlorophenol, 3-chlorophenol, 4-chlorophenol, 2-bromophenol, 3-bromophenol, 4-bromophenol, 2-iodophenol, 3-iodophenol, 4-iodophenol, 2,6-difluorophenol, 3,5-difluorophenol, 2,6-dichlorophenol, 3,5-dichlorophenol, 2,6-dibromophenol, 3,5-dibromophenol, 2,6-diiodophenol, 3,5-diiodophenol, 2,4,6-trifluorophenol, 3,4,5-trifluorophenol, 2,4,6-trichlorophenol, 2,4,6-tribromophenol, 2,4,6-triiodophenol, pentafluorophenol, pentachlorophenol, pentabromophenol, pentaiodophenol, 2-(trifluoromethyl)phenol, 3-(trifluoromethyl)phenol, 4-(trifluoromethyl)phenol, 2,6-bis(trifluoromethyl)phenol, 3,5-bis(trifluoromethyl)phenol, 2-cyanophenol, 3-cyanophenol, 4-cyanophenol, 2-nitrophenol, 3-nitrophenol and 4-nitrophenol.

When the compound (b) is a thiophenol compound, examples thereof are thiophenol compounds in which an oxygen atom is replaced with a sulfur atom in the above-mentioned phenol compounds.

When the compounds (b) is a carboxylic acid, examples thereof are 2-fluorobenzoic acid, 3-fluorobenzoic acid, 4-fluorobenzoic acid, 2,3-difluorobenzoic acid, 2,4-difluorobenzoic acid, 2,5-difluorobenzoic acid, 2,6-difluorobenzoic acid, 2,3,4-trifluorobenzoic acid, 2,3,5-trifluorobenzoic acid, 2,3,6-trifluorobenzoic acid, 2,4,5-trifluorobenzoic acid, 2,4,6-trifluorobenzoic acid, 2,3,4,5-tetrafluorobenzoic acid, 2,3,4,6-tetrafluorobenzoic acid, pentafluorobenzoic acid, fluoroacetic acid, difluoroacetic acid, trifluoroacetic acid, pentafluoropropanoic acid, heptafluorobutanoic acid and 1,1-bis(trifluoromethyl)-2,2,2-trifluoroehtanoic acid.

When the compounds (b) is a sulfonic acid, examples thereof are fluoromethanesulfonic acid, difluoromethanesulfonic acid, trifluoromethanesulfonic acid, pentafluoroethanesulfonic acid, heptafluoropropanesulfonic acid, and 1,1-bis(trifluoromethyl)-2,2,2-trifluoroehtanesulfonic acid.

A preferable amine of the compound (b) is bis(trifluoromethyl)amine, bis(2,2,2-trifluoromethyl)amine, bis(2,2,3,3,3-pentafluoropropyl)amine, bis(2,2,2-trifluoro-1-trifluoromethylethyl)amine, bis(1,1-bis(trifluoromethyl)-2,2,2-trifluoroethyl)amine or bis(pentafluorophenyl)amine; preferable alcohols thereof are trifluoromethanol, 2,2,2-trifluoroethanol, 2,2,3,3,3-pentafluoropropanol, 2,2,2-trifluoro-1-trifluoromethylethanol or 1,1-bis(trifluoromethyl)-2,2,2-trifluoroethanol; a preferable phenol thereof is 2-fluorophenol, 3-fluorophenol, 4-fluorophenol, 2,6-difluorophenol, 3,5-difluorophenol, 2,4,6-trifluorophenol, 3,4,5-trifluorophenol, pentafluorophenol, 2-(trifluoromethyl)phenol, 3-(trifluoromethyl)phenol, 4-(trifluoromethyl)phenol, 2,6-bis(trifluoromethyl)phenol, 3,5-bis(trifluoromethyl)phenol or 2,4,6-tris(trifluoromethyl)phenol; a preferable carboxylic acid thereof is pentafluorobenzoic acid or trifluoroacetic acid; and a preferable sulfonic acid thereof is trifluoromethanesulfonic acid.

A more preferable compound (b) is bis(trifluoromethyl)amine, bis(pentafluorophenyl)amine, trifluoromethanol, 2,2,2-trifluoro-1-trifluoromethylethanol, 1,1-bis(trifluoromethyl)-2,2,2-trifluoroethanol, 4-fluorophenol, 2,6-difluorophenol, 2,4,6-trifluorophenol, 3,4,5-trifluorophenol, pentafluorophenol, 4-(trifluoromethyl)phenol, 2,6-bis(trifluoromethyl)phenol or 2,4,6-tris(trifluoromethyl)phenol; and a further preferable compound (b) is 3,4,5-trifluorophenol, pentafluorophenol or 1,1-bis(trifluoromethyl)-2,2,2-trifluoroethanol.

Examples of J in the above formula [3] are a boron atom, an aluminum atom, a gallium atom, an indium atom and a thallium atom. J is preferably a boron atom or an aluminum atom, and particularly preferably a boron atom.

In the above formula [3], n is 2 or 3, and preferably 2.

Examples of the hydrocarbon group as $R^2$ in the above formula [3] are the hydrocarbon groups mentioned above as $L^1$ in the above formula [1], and the halogenated hydrocarbon groups mentioned above as $R^1$ in the above formula [2]. Preferred is an alkyl group or an aryl group; and more preferred is a methyl group, an ethyl group, a n-propyl group, an isopropyl group, a n-butyl group, a sec-butyl group, a tert-butyl group, an isobutyl group, a n-pentyl group, a n-hexyl group, a n-heptyl group, a n-octyl group, a n-decyl group, a n-dodecyl group, a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a n-propylphenyl group, an isopropylphenyl group, a n-butylphenyl group, a sec-butylphenyl group, a tert-butylphenyl group, an isobutylphenyl group, a n-pentylphenyl group, a n-hexylphenyl group, a n-octylphenyl group, a n-decylphenyl group, a n-dodecylphenyl group, a n-tetradecylphenyl group, a naphthyl group, an anthracenyl group, a 2-fluorophenyl group, a 3-fluorophenyl group, a 4-fluorophenyl group, a 2,4-difluorophenyl group, a 2,6-difluorophenyl group, a 3,4-difluorophenyl group, a 3,5-difluorophenyl group, a 2,4,6-trifluorophenyl group, a 2,3,5,6-tetrafluorophenyl group, or a pentafluorophenyl group. Further preferred is a methyl group, an ethyl group, a n-propyl group, an isopropyl group, a n-butyl group, a sec-butyl group, a tert-butyl group, an isobutyl group, a n-hexyl group, a n-octyl group, a n-dodecyl group, a phenyl group, a 2-tolyl group, a 2,4,6-trimethylphenyl group, a n-propylphenyl group, a n-butylphenyl group, a tert-butylphenyl group, a n-pentylphenyl group, a n-hexylphenyl group, a n-octylphenyl group, a n-decylphenyl group, a n-dodecylphenyl group, a naphthyl group, an anthracenyl group, a 2-fluorophenyl group, a 3-fluorophenyl group, a 4-fluorophenyl group, a 2,4-difluorophenyl group, a 2,6-difluorophenyl group, a 3,4-difluorophenyl group, a 3,5-difluorophenyl group, a 2,4,6-trifluorophenyl group, or a pentafluorophenyl group. Particularly preferred is a methyl group, a phenyl group, or a pentafluorophenyl group.

Examples of the compound (c) represented by the formula [3] are methylboric acid, ethylboric acid, n-propylboric acid, isopropylboric acid, n-butylboric acid, sec-butylboric acid, tert-butylboric acid, isobutylboric acid, n-pentylboric acid, n-hexylboric acid, n-heptylboric acid, n-octylboric acid, n-decylboric acid, n-dodecylboric acid, phenylboric acid, 2-tolylboric acid, 3-tolylboric acid, 4-tolylboric acid, 2,3-xylylboric acid, 2,4-xylylboric acid, 2,5-xylylboric acid, 2,6-xylylboric acid, 3,4-xylylboric acid, 3,5-xylylboric acid, 2,3,4-trimethylphenylboric acid, 2,3,5-trimethylphenylboric acid, 2,3,6-trimethylphenylboric acid, 2,4,6-trimethylphenylboric acid, 3,4,5-trimethylphenylboric acid, n-propylphenylboric acid, isopropylphenylboric acid, n-butylphenylboric acid, sec-butylphenylboric acid, tert-butylphenylboric acid, Isobutylphenylboric acid, n-pentylphenylboric acid, n-hexylphenylboric acid, n-octylphenylboric acid, n-decylphenylboric acid, n-dodecylphenylboric acid, n-tetradecylphenylboric acid, naphthylboric acid, anthracenylboric acid, 2-fluorophenylboric acid, 3-fluorophenylboric acid, 4-fluorophenylboric acid, 2,4-difluorophenylboric acid, 2,6-difluorophenylboric acid, 3,4-difluorophenylboric acid, 3,5-difluorophenylboric acid, 2,4,6-trifluorophenylboric acid, 2,3,5,6-tetrafluorophenylboric acid, and pentafluorophenylboric acid.

The compound (c) is preferably methylboric acid, ethylboric acid, n-propylboric acid, isopropylboric acid, n-butylboric acid, sec-butylboric acid, tert-butylboric acid, isobutylboric acid, n-hexylboric acid, n-octylboric acid, n-dodecylboric acid, phenylboric acid, 2-tolylboric acid, 2,4,6-trimethylphenylboric acid, n-propylphenylboric acid, n-butylphenylboric acid, tert-butylphenylboric acid, n-pentylphenylboric acid, n-hexylphenylboric acid, n-octylphenylboric acid, n-decylphenylboric acid, n-dodecylphenylboric acid, naphthylboric acid, anthracenylboric acid, 2-fluorophenylboric acid, 3-fluorophenylboric acid, 4-fluorophenylboric acid, 2,4-difluorophenylboric acid, 2,6-difluorophenylboric acid, 3,4-difluorophenylboric acid, 3,5-difluorophenylboric acid, 2,4,6-trifluorophenylboric acid, or pentafluorophenylboric acid. Particularly preferred is methylboric acid, phenylboric acid, or pentafluorophenylboric acid.

A method for contacting the compounds (a) to (c) is not particularly limited. Examples thereof are as follows.

① A method of contacting (c) after contacting (a) and (b).
② A method of contacting (b) after contacting (a) and (c).
③ A method of contacting (a) after contacting (b) and (c).

Preferred is ① or ②. Namely, the metal compound according to the present invention is preferably obtained by contacting (c) with a contact product obtained by contacting (a) and (b), or by contacting (b) with a contact product obtained by contacting (a) and (c). Further, there may be carried out either a method comprising the steps of:

(1) contacting (a) and (b), (a) and (c), or (b) and (c) to obtain a contact product, and (2) contacting the contact product with the remaining compound, or a method comprising the steps of:

(1) contacting (a) and (b), (a) and (c), or (b) and (c) to obtain a contact product, (2) purifying the contact product to obtain a purified contact product, and (3) contacting the purified contact product with the remaining compound.

The contact treatment of the above-mentioned compounds (a) to (c) is preferably carried out under an inert gas atmosphere. The treatment temperature is usually from −100 to 300° C., preferably from −80 to 200° C., and further preferably from 0 to 150° C. The treatment time is usually from 1 minute to 200 hours, and preferably from 10 minutes to 100 hours. Further, a solvent may be used in the treatment, or these compounds may be directly contact-treated using no solvent. There can be used any solvent selected from a non-polar solvent such as an aliphatic hydrocarbon solvent and an aromatic hydrocarbon solvent, and a polar solvent such as a halogenated solvent and an etheral solvent, which is inert to the compounds (a) to (c). Examples of the solvent are butane, pentane, hexane, heptane, octane, 2,2,4-trimethylpentane, cyclohexane, benzene, toluene, xylene, dichloromethane, difluoromethane, chloroform, 1,2-dichloroethane, 1,2-dibromoethane, 1,1,2-trichloro-1,2,2-trifluoroethane, tetrachloroethylene, chlorobenzene, bromobenzene, o-dichlorobenzene, dimethyl ether, diethyl ether, diisopropyl ether, di-n-butyl ether, methyl tert-butyl ether, anisole, 1,4-dioxane, 1,2-dimethoxyethane, bis(2-methoxyethyl) ether, tetrahydrofuran and tetrahydropyran.

The compound (b) is used in an amount of preferably from 0.1 to 8 mol, more preferably from 1 to 6 mol, further preferably from 2 to 4 mol, and particularly preferably from 2.5 to 3.5 mol, per one mol of the compound (a).

The compound (c) is used in an amount of preferably from 0.6 to 8 mol, more preferably from 0.7 to 6 mol, further preferably from 0.8 to 4 mol, and particularly preferably from 0.9 to 1.2 mol, per one mol of the compound (a).

As a result of the contact treatment, at least one of compounds (a) to (c), which are raw materials, may remain as an unreacted matter in the metal compound according to the present invention.

When the compounds (a) to (c) are triphenyl bismuth, pentafluorophenol and pentafluorophenylboric acid, respectively, an example of a process for producing the metal compound according to the present inveniton comprises the steps of:

(1) adding dropwise a toluene solution containing pentafluorophenol in amount of three times by mole to triphenyl bismuth to a toluene solution of triphenyl bismuth, (2) stirring for from 10 minutes to 24 hours at room temperature, (3) stirring under a refluxing condition for from 10 minutes to 24 hours, (4) concentrating the solution, (5) filtering a precipitated solid component, (6) drying the solid component, (7) adding toluene and pentafluorophenylboric acid acid to the obtained solid component, and (8) stirring under a refluxing condition for from 10 minutes to 24 hours.

The metal compound (hereinafter, referred to as "compound (A)") according to the present invention can preferably be used as a catalyst component of a catalyst for addition polymerization. Examples of the catalyst for addition polymerization using said catalyst component are (1) a catalyst obtained by a process comprising the step of contacting the compound (A) with the compound (B), and (2) a catalyst obtained by a process comprising the step of contacting the compound (A) with the compound (B) and the compound (C). In order to obtain a catalyst having a high polymerization activity, the above latter catalyst is preferable.

Preferable examples of the compound (B) are a metal compound represented by the following formula [4], and a μ-oxo type metal compound thereof:

    [4], wherein a is a number satisfying $0<a\leq8$; b is a number satisfying $0<b\leq8$; M is a metal atom of the Groups 3 to 12 or Lanthanide Series of the Periodic Table of the Elements; $L^2$ is a group having a cyclopentadienyl type anion skeleton, or a group containing a hetero-atom, a plurality of $L^2$ groups may be the same or different each other, and a plurality of $L^2$ groups may be optionally linked in direct, or through a group containing a carbon atom, a silicon atom, a nitrogen atom, an oxygen atom, a sulfur atom or a phosphorus atom; $X^1$ is a halogen atom, a hydrocarbon group (excluding the group having a cyclopentadienyl type anion skeleton) or a hydrocarbonoxy group, and a plurality of $X^1$ groups may be the same or different each other.

Examples of M are a scandium atom, an yttrium atom, a titanium atom, a zirconium atom, a hafnium atom, a vanadium atom, a niobium atom, a tantalum atom, a chromium atom, an iron atom, a ruthenium atom, a cobalt atom, a rhodium atom, a nickel atom, a palladium atom, a samarium atom and an ytterbium atom. $M^2$ is preferably a metal atom of Groups 3 to 11, and particularly preferably a titanium atom, a zirconium atom or a hafnium atom.

Examples of the group having a cyclopentadienyl type anion skeleton as $L^2$ are an $\eta^5$-(substituted)cyclopentadienyl group, an $\eta^5$-(substituted)indenyl group, and an $\eta^5$-(substituted)fluorenyl group. Specific examples thereof are an $\eta^5$-cyclopentadienyl group, an $\eta^5$-methylcyclopentadienyl group, an $\eta^5$-tert-butylcyclopentadienyl group, an $\eta^5$-1,2-dimethylcyclopentadienyl group, an $\eta^5$-1,3-dimethylcyclopentadienyl group, an $\eta^5$-1-tert-butyl-2-methylcyclopentadienyl group, an $\eta^5$-1-tert-butyl-3-methylcyclopentadienyl group, an $\eta^5$-1-methyl-2-isopropylcyclopentadienyl group, an $\eta^5$-1-methyl-3-isopropylcyclopentadienyl group, an $\eta^5$-1,2,3-trimethylcyclopentadienyl group, an $\eta^5$-1,2,4-trimethylcyclopentadienyl group, an $\eta^5$-tetramethylcyclopentadienyl group, an $\eta^5$-pentamethylcyclopentadienyl group, an $\eta^5$-indenyl group, an $\eta^5$-4,5,6,7-tetrahydroindenyl group, an $\eta^5$-2-methylindenyl group, an $\eta^5$-3-methylindenyl group, an $\eta^5$-4-methylindenyl group, an $\eta^5$-5-methylindenyl group, an $\eta^5$-6-methylindenyl group, an $\eta^5$-7-methylindenyl group, an $\eta^5$-2-tert-butylindenyl group, an $\eta^5$-3-tert-butylindenyl group, an $\eta^5$-4-tert-butylindenyl group, an $\eta^5$-5-tert-butylindenyl group, an $\eta^5$-6-tert-butylindenyl group, an $\eta^5$-7-tert-butylindenyl group, an $\eta^5$-2,3-dimethylindenyl group, an $\eta^5$-4,7-dimethylindenyl group, an $\eta^5$-2,4,7-trimethylindenyl group, an $\eta^5$-2-methyl-4-isopropylindenyl group, an $\eta^5$-4,5-benzindenyl group, an $\eta^5$-2-methyl-4,5-benzindenyl group, an $\eta^5$-4-phenylindenyl group, an $\eta^5$-2-methyl-5-phenylindenyl group, an $\eta^5$-2-methyl-4-phenylindenyl group, an $\eta^5$-2-methyl-4-naphthylindenyl group, an $\eta^5$-fluorenyl group, an $\eta^5$-2,7-dimethylfluorenyl group and an $\eta^5$-2,7-di-tert-butylfluorenyl group; and substitution groups thereof.

Examples of the hetero-atom in the group containing a hetero-atom as $L^2$ are an oxygen atom, a sulfur atom, a nitrogen atom and a phosphorus atom. Examples of the group containing a hetero-atom are an alkoxy group; an aryloxy group; a thioalkoxy group; a thioaryloxy group; an alkylamino group; an arylamino group; an alkylphosphino group; an arylphosphino group; an aromatic or aliphatic heterocyclic group containing in its ring at least one atom selected from the group consisting of an oxygen atom, a sulfur atom, a nitrogen atom and a phosphorus atom; and a chelating ligand.

Examples of the group containing a hetero-atom are a methoxy group, an ethoxy group, a n- or iso-propoxy group, a n-, sec-, iso- or tert-butoxy group, a phenoxy group, a 2-methylphenoxy group, a 2,6-dimethylphenoxy group, a 2,4,6-trimethylphenoxy group, a 2-ethylphenoxy group, a 4-n-propylphenoxy group, a 2-isopropylphenoxy group, a 2,6-diisopropylphenoxy group, a 4-sec-butylphenoxy group, a 4-tert-butylphenoxy group, a 2,6-di-sec-butylphenoxy group, a 4-tert-butyl-4-methylphenoxy group, a 2,6-di-tert-butylphenoxy group, a 4-methoxyphenoxy group, a 2,6-dimethoxyphenoxy group, a 3,5-dimethoxyphenoxy group, a 2-chlorophenoxy group, a 4-nitrosophenoxy group, a 4-nitrophenoxy group, a 2-aminophenoxy group, a 3-aminophenoxy group, a 4-aminothiophenoxy group, a 2,3,6-trichlorophenoxy group, a 2,4,6-trifluorophenoxy group, a thiomethoxy group, a dimethylamino group, a diethylamino group, a di-n- or iso-propylamino group, a diphenylamino group, an isopropylamino group, a tert-butylamino group, a pyrrolyl group, a dimethylphosphino group, a 2-(2-oxy-1-propyl)phenoxy group, a catecholato group, a 2-hydroxyphenoxy group, a resorcinolate group, a 3-hydroxyphenoxy group, a 4-isopropyl-catecholato group, a 2-hydroxy-4isopropyl-phenoxy group, a 3-methoxycatecholato group, a 2-hydroxy-3-methoxyphenoxy group, a 1,8-dihydroxynahpthyl group, a 1,2-dihydroxynahpthyl group, a 2,2'-biphenyldiol group, a 1,1'-bi-2-naphthol group, a 2,2'-dihydroxy-6,6'-dimethylbiphenyl group, a 4,4',6,6'-tetra-tert-butyl-2,2'-methylenediphenoxy group, and a 4,4',6,6'-tetramethyl-2,2'-isobutylidenediphenoxy group.

A further example of the hetero atom-containing group is a group represented by the following formula [5]:

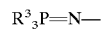    [5]

wherein $R^3$ is a hydrogen atom, a halogen atom or a hydrocarbon group, three $R^3$ groups may be the same or different, and two or more thereof may be bonded mutually, or may form a ring.

Examples of $R^3$ in the formula [5] are a hydrogen atom, a fluorine atom, a chlorine atom, a bromine atom, an iodine atom, a methyl group, an ethyl group, a n-propyl group, an isopropyl group, a n-butyl group, a tert-butyl group, a cyclohexyl group, a phenyl group, a 1-naphthyl group and a benzyl group.

A still further example of the hetero atom-containing group is a group represented by the following formula [6]:

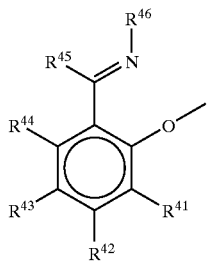

[6]

wherein respective $R^{41}$ to $R^{46}$ groups are independently a hydrogen atom, a halogen atom, a hydrocarbon group, a hydrocarbon oxy group, a silyl group or an amino group, they may be the same or different, and two or more thereof may be bonded mutually, or may form a ring.

Examples of $R^{41}$ to $R^{46}$ in the above formula [6] are a hydrogen atom, a fluorine atom, a chlorine atom, a bromine atom, an iodine atom, a phenyl group, a 1-naphtyl group, a 2-naphtyl group, a tert-butyl group, a 2,6-dimethylphenyl group, a 2-fluorenyl group, a 2-methylphenyl group, a 4-trifluoromethylphenyl group, a 4-methoxyphenyl group, a 4-pyridyl group, a cyclohexyl group, a 2-isopropylphenyl group, a benzyl group, a methyl group, a triethylsilyl group, a diphenylmethylsilyl group, a 1-methy-1-phenylethyl group, a 1,1-dimethyl propyl group, a 2-chlorophenyl group and a pentafluorophenyl group.

The above-mentioned chelating ligand as $L^2$ means a ligand having plural coordinating positions. Examples thereof are acetylacetonate, diimine, oxazoline, bisoxazoline, terpyridine, acylhydrazone, diethylenetriamine, triethylenetetramine, porphyrin, crown ether and cryptate.

Examples of the heterocyclic group as $L^2$ are a pyridyl group, an N-substituted imidazolyl group and an N-substituted indazolyl group, and preferred is a pyridyl group.

Examples of the above-mentioned group, through which plural $L^2$ groups are linked, are an alkylene group such as a methylene group, an ethylene group and a propylene group; a substituted alkylene group such as a dimethylmethylene group (an isopropylidene group) and a diphenylmethylene group; a silylene group; a substituted silylene group such as a dimethylsilylene group, a diethylsilylene group, a diphenylsilylene group, a tetramethyldisilylene group and a dimethoxysilylene group; and a hetero-atom such as a nitrogen atom, an oxygen atom, a sulfur atom and a phosphorus atom. Among them, particularly preferred is a methylene group, an ethylene group, a dimethylmethylene group (an isopropylidene group), a diphenylmethylene group, a dimethylsilylene group, a diethylsilylene group, a diphenylsilylene group or a dimethoxysilylene group.

Examples of the halogen atom as $X^1$ are a fluorine atom, a chlorine atom, a bromine atom and an iodine atom. Examples of the hydrocarbon group as $X^1$ are an alkyl group, an aralkyl group, an aryl group and an alkenyl group.

Examples of the alkyl group as $X^8$ are a methyl group, an ethyl group, a n-propyl group, an isopropyl group, a n-butyl group, a sec-butyl group, a tert-butyl group, an isobutyl group, a n-pentyl group, a neopentyl group, an amyl group, a n-hexyl group, a n-octyl group, a n-decyl group, a n-dodecyl group, a n-pentdecyl group and a n-eicosyl group.

Each of these alkyl groups may be substituted with a halogen atom such as a fluorine atom, a chlorine atom, a bromine atom and an iodine atom. Examples of such an alkyl group are a fluoromethyl group, a trifluoromethyl group, a chloromethyl group, a trichloromethyl group, a fluoroethyl group, a pentafluoroethyl group, a perfluoropropyl group, a perfluorobutyl group, a perfluorohexyl group, a perfluorooctyl group, a perchloropropyl group, a perchlorobutyl group and a perbromopropyl group.

Further, these alkyl groups may be substituted with an alkoxy group such as a methoxy group and an ethoxy group; an aryloxy group such as a phenoxy group; or an aralkyloxy group such as a benzyloxy group.

The alkyl group as $X^1$ is preferably an alkyl group having 1 to 20 carbon atoms, and more preferably a methyl group, an ethyl group, an isopropyl group, a tert-butyl group, an isobutyl group or an amyl group.

Examples of the aralkyl group as $X^1$ are a benzyl group, a (2-methylphenyl)methyl group, a (3-methylphenyl)methyl group, a (4-methylphenyl)methyl group, a (2,3-dimethylphenyl)methyl group, a (2,4-dimethylphenyl)methyl group, a (2,5-dimethylphenyl)methyl group, a (2,6-dimethylphenyl)methyl group, a (3,4-dimethylphenyl)methyl group, a (3,5-dimethylphenyl)methyl group, a (2,3,4-timethylphenyl)methyl group, a (2,3,5-timethylphenyl)methyl group, a (2,3,6-timethylphenyl)methyl group, a (3,4,5-timethylphenyl)methyl group, a (2,4,6-timethylphenyl)methyl group, a (2,3,4,5-tetramethylphenyl)methyl group, a (2,3,4,6-tetramethylphenyl)methyl group, a (2,3,5,6-tetramethylphenyl)methyl group, a (pentamethylphenyl)methyl group, an (ethylphenyl)methyl group, a (n-propylphenyl) methyl group, an (isopropylphenyl)methyl group, a (n-butylphenyl)methyl group, a (sec-butylphenyl)methyl group, a (tert-butylphenyl)methyl group, a (n-pentylphenyl)methyl group, a (neopentylphenyl)methyl group, a (n-hexylphenyl) methyl group, a (n-octylphenyl)methyl group, a (n-decylphenyl)methyl group, a (tetradecylphenyl)methyl group, a naphthylmethyl group and an anthracenylmethyl group.

Each of these aralkyl groups may be substituted with a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

The aralkyl group as $X_1$ is preferably an aralkyl group having 7 to 20 carbon atoms, and more preferably a benzyl group.

Examples of the aryl group as $X^1$ are a phenyl group, a 2-tolyl group, a 3-tolyl group, a 4-tolyl group, a 2,3-xylyl group, a 2,4-xylyl group, a 2,5-xylyl group, a 2,6-xylyl group, a 3,4-xylyl group, a 3,5-xylyl group, a 2,3,4-trimethylphenyl group, a 2,3,5-trimethylphenyl group, a 2,3,6-trimethylphenyl group, a 2,4,6-trimethylphenyl group, a 3,4,5-trimethylphenyl group, a 2,3,4,5-tetramethylphenyl group, a 2,3,4,6-tetramethylphenyl group, a 2,3,5,6-tetramethylphenyl group, a pentamethylphenyl group, an ethylphenyl group, a n-propylphenyl group, an isopropylphenyl group, a n-butylphenyl group, a sec-butylphenyl group, a tert-butylphenyl group, an isobutylphenyl group, a n-pentylphenyl group, a neopentylphenyl group, a n-hexylphenyl group, a n-octylphenyl group, a n-decylphenyl group, a n-dodecylphenyl group, a n-tetradecylphenyl group, a naphthyl group and an anthracenyl group.

Each of these aryl groups may be substituted with a halogen atom such as a fluorine atom, a chlorine atom, a bromine atom and an iodine atom; an alkoxy group such as a methoxy group and an ethoxy group; an aryloxy group such as a phenoxy group; or an aralkyloxy group such as a benzyloxy group.

The aryl group is preferably an aryl group having 6 to 20 carbon atoms, and more preferably a phenyl group.

Examples of the alkenyl group as $X^1$ are an ally group, a methally group, a crotyl group and a 1,3-diphenyl-2-propenyl group. The alkenyl group is preferably an alkenyl group having 3 to 20 carbon atoms, and more preferably an ally group or a methally group.

Examples of the hydrocarbonoxy group as $X^1$ are an alkoxy group, an aryloxy group and an aralkyloxy group. Preferred is an alkoxy group having 1 to 20 carbon atoms, an aryloxy group having 6 to 20 carbon atoms, or an aralkyloxy group having 7 to 20 carbon atoms. Examples thereof are hydrocarbonoxy groups as above-exemplified as $L^1$, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group and a benzyloxy group. More preferred is a methoxy group, an ethoxy group, an isopropoxy group, a tert-butyl group, an isobutoxy group, a phenoxy group, a 2,6-di(tert-butyl)phenoxy group or a benzyloxy group; further preferred is a methoxy group, a phenoxy group, a 2,6-di(tert-butyl)phenoxy group or a benzyloxy group; and particularly preferred is a methoxy group or a phenoxy group.

$X^1$ is more preferably a chlorine atom, a methyl group, an ethyl group, a n-propyl group, an isopropyl group, a n-butyl group, a benzyl group, an allyl group, a methallyl group, a methoxy group, an ethoxy group or a phenoxy group, and further preferably a chlorine atom, a methyl group, a methoxy group or a phenoxy group.

In the formula [4], respective numbers of a and b depend upon the valency of M.

Examples of the metal compound represented by the formula [4], wherein M is a titanium atom, are dimethylsilylenebis(cyclopentadienyl)titanium dichloride, dimethylsilylenebis(2-methylcyclopentadienyl)titanium dichloride, dimethylsilylenebis(3-methylcyclopentadienyl)titanium dichloride, dimethylsilylenebis(2-n-butylcyclopentadienyl)titanium dichloride, dimethylsilylenebis(3-n-butylcyclopentadienyl)titanium dichloride, dimethylsilylenebis(2,3-dimethylcyclopentadienyl)titanium dichloride, dimethylsilylenebis(2,4-dimethylcyclopentadienyl)titanium dichloride, dimethylsilylenebis(2,5-dimethylcyclopentadienyl)titanium dichloride, dimethylsilylenebis(3,4-dimethylcyclopentadienyl)titanium dichloride, dimethylsilylenebis(2,3-ethylmethylcyclopentadienyl)titanium dichloride, dimethylsilylenebis(2,4-ethylmethylcyclopentadienyl)titanium dichloride, dimethylsilylenebis(2,5-ethylmethylcyclopentadienyl)titanium dichloride, dimethylsilylenebis(3,5-ethylmethylcyclopentadienyl)titanium dichloride, dimethylsilylenebis(2,3,4-trimethylcyclopentadienyl)timium dichloride, dimethylsilylenebis(2,3,5-trimethylcyclopentadienyl)titanium dichloride, dimethylsilylenebis(tetramethylcyclopentadienyl)titanium dichloride, dimethylsilylenebis(indenyl)titanium dichloride, dimethylsilylenebis(4,5,6,7-tetrahydroindenyl)titanium dichloride, dimethylsilylene(cyclopentadienyl)(indenyl)titanium dichloride, dimethylsilylene(methylcyclopentadienyl)(indenyl)titanium dichloride, dimethylsilylene(n-butylcyclopentadienyl)(indenyl)titanium dichloride, dimethylsilylene(tetramethylcyclopentadienyl)(indenyl)titanium dichloride, dimethylsilylene(cyclopentadienyl)(fluorenyl)titanium dichloride, dimethylsilylene(methylcyclopentadienyl)(fluorenyl)titanium dichloride, dimethylsilylene(n-butylcyclopentadienyl)(fluorenyl)titanium dichloride, dimethylsilylene (tetramethylcyclopentadienyl)(fluorenyl)titanium dichloride, and dimethylsilylene(indenyl)(fluorenyl)titanium dichloride; and compounds obtained by changing "dimethylsilylene" in the above compounds to "diethylsilylene", "diphenylsilylene" or "dimethoxysilylene".

Further examples of the metal compound represented by the formula [4], wherein M is a titanium atom, are bis(cyclopentadienyl)titanium dichloride, bis(methylcyclopentadienyl)titanium dichloride, bis(n-butylcyclopentadienyl)titanium dichloride, bis(dimethylcyclopentadienyl)titanium dichloride, bis(ethylmethylcyclopentadienyl)titanium dichloride, bis(trimethylcyclopentadienyl)titanium dichloride, bis(tetramethylcyclopentadienyl)titanium dichloride, bis(pentamethylcyclopentadienyl)titanium dichloride, bis(indenyl)titanium dichloride, bis(4,5,6,7-tetrahydroindenyl)titanium dichloride, bis(fluorenyl)titanium dichloride, bis(2-phenylindenyl)titanium dichloride, bis[2-(bis-3,5-trifluoromethylphenyl)indenyl]titanium dichloride, bis[2-(4-tert-butylphenyl)indenyl]titanium dichloride, bis[2-(4-trifluoromethylphenyl)indenyl]titanium dichloride, bis[2-(4-methylphenyl)indenyl]titanium dichloride, bis[2-(3,5-dimethylphenyl)indenyl]titanium dichloride, bis[2-(pentafluorophenyl)indenyl]titanium dichloride, cyclopentadienyl(pentamethylcyclopentadienyl)titanium dichloride, cyclopentadienyl(indenyl)titanium dichloride, cyclopentadienyl(fluorenyl)titanium dichloride, indenyl (fluorenyl)titanium dichloride, pentamethylcyclopentadienyl(indenyl)titanium dichloride, pentamethylcyclopentadienyl(fluorenyl)titanium dichloride, cyclopentadienyl(2-phenylindenyl)titanium dichloride, pentamethylcyclopentadienyl(2-phenylindenyl)titanium dichloride, ethylenebis(cyclopentadienyl)titanium dichloride, ethylenebis(2-methylcyclopentadienyl)titanium dichloride, ethylenebis(3-methylcyclopentadienyl)titanium dichloride, ethylenebis(2-n-butylcyclopentadienyl)titanium dichloride, ethylenebis(3-n-butylcyclopentadienyl)titanium dichloride, ethylenebis(2,3-dimethylcyclopentadienyl)titanium dichloride, ethylenebis(2,4-dimethylcyclopentadienyl) titanium dichloride, ethylenebis(2,5-dimethylcyclopentadienyl)titanium dichloride, ethylenebis(3,4-dimethylcyclopentadienyl)titanium dichloride, ethylenebis(2,3-ethylmethylcyclopentadienyl)titanium dichloride, ethylenebis(2,4-ethylmethylcyclopentadienyl)titanium dichloride, ethylenebis(2,5-ethylmethylcyclopentadienyl)titanium dichloride, ethylenebis(3,5-ethylmethylcyclopentadienyl)titanium dichloride, ethylenebis(2,3,4-trimethylcyclopentadienyl)titanium dichloride, ethylenebis(2,3,5-trimethylcyclopentadienyl)titanium dichloride, ethylenebis(tetramethylcyclopentadienyl)titanium dichloride, ethylenebis(indenyl)titanium dichloride, ethylenebis(4,5,6,7-tetrahydroindenyl)titanium dichloride, ethylenebis(2-phenylindenyl)titanium dichloride, ethylenebis(fluorenyl)titanium dichloride, ethylene(cyclopentadienyl)(pentamethylcyclopentadienyl)titanium dichloride, ethylene (cyclopentadienyl)(indenyl)titanium dichloride, ethylene (methylcyclopentadienyl)(indenyl)titanium dichloride, ethylene(n-butylcyclopentadienyl)(indenyl)titanium dichloride, ethylene(tetramethylcyclopentadienyl)(indenyl)titanium dichloride, ethylene(cyclopentadienyl)(fluorenyl)titanium dichloride, ethylene(methylcyclopentadienyl)(fluorenyl)titanium dichloride, ethylene (pentamethylcyclopentadienyl)(fluorenyl)titanium dichloride, ethylene(n-butylcyclopentadienyl)(fluorenyl)titanium dichloride, ethylene(tetramethylpentadienyl)(fluorenyl)titanium dichloride, ethylene(indenyl)(fluorenyl)titanium dichloride, isopropylidenebis(cyclopentadienyl)titanium dichloride, isopropylidenebis(2-methylcyclopentadienyl)titanium dichloride, isopropylidenebis(3-methylcyclopentadienyl)titanium dichloride, isopropylidenebis(2-n-butylcyclopentadienyl)titanium dichloride, isopropylidenebis(3-n-butylcyclopentadienyl)titanium dichloride, isopropylidenebis(2,3-dimethylcyclopentadienyl)titanium dichloride, isopropylidenebis(2,4-dimethylcyclopentadienyl)titanium dichloride, isopropylidenebis(2,5-dimethylcyclopentadienyl)titanium dichloride, isopropylidenebis(3,4-dimethylcyclopentadienyl)titanium dichloride, isopropylidenebis(2,3-ethylmethylcyclopentadienyl)titanium dichloride, isopropylidenebis(2,4-ethylmethylcyclopentadienyl)titanium dichloride, isopropylidenebis(2,5-ethylmethylcyclopentadienyl)titanium dichloride, isopropylidenebis(3,5-ethylmethylcyclopentadienyl)titanium dichloride, isopropylidenebis(2,3,4-trimethylcyclopentadienyl)titanium dichloride, isopropylidenebis(2,3,5-trimethylcyclopentadienyl)titanium dichloride, isopropylidenebis(tetramethylcyclopentadienyl)titanium dichloride, isopropylidenebis(indenyl)titanium dichloride, isopropylidenebis(4,5,6,7-tetrahydroindenyl)titanium dichloride, isopropylidenebis(2-phenylindenyl)titanium dichloride, isopropylidenebis(fluorenyl)titanium dichloride, isopropylidene(cyclopentadienyl)(tetramethylcyclopentadienyl)titanium dichloride, isopropylidene(cyclopentadienyl)(indenyl)titanium dichloride, isopropylidene(methylcyclopentadienyl)(indenyl)titanium dichloride, isopropylidene(n-butylcyclopentadienyl)(indenyl)titanium dichloride, isopropylidene(tetramethylcyclopentadienyl)(indenyl)titanium dichloride, isopropylidene(cyclopentadienyl)(fluorenyl)titanium dichloride, isopropylidene(methylcyclopentadienyl)(fluorenyl)titanium dichloride, isopropylidene(n-butylcyclopentadienyl)(fluorenyl)titanium dichloride, isopropylidene(tetramethylcyclopentadienyl)(fluorenyl)titanium dichloride, isopropylidene(indenyl)(fluorenyl)titanium dichloride, cyclopentadienyl(dimethylamido)titanium dichloride, cyclopentadienyl(phenoxy)titanium dichloride, cyclopentadienyl(2,6-dimethylphenyl)titanium dichloride, cyclopentadienyl(2,6-diisopropylphenyl)titanium dichloride, cyclopentadienyl(2,6-di-tert-butylphenyl)titanium dichloride, pentamethylcyclopentadienyl(2,6-dimethylphenyl)titanium dichloride, pentamethylcyclopentadienyl(2,6-diisopropylphenyl)titanium dichloride, pentamethylcyclopentadienyl(2,6-di-tert-butylphenyl)titanium dichloride, indenyl(2,6-diisopropylphenyl)titanium dichloride, fluorenyl (2,6-diisopropylphenyl)titanium dichloride, (tert-butylamido)tetramethylcyclopentadienyl-1,2-ethanediyltitanium dichloride, (methylamido)tetramethylcyclopentadienyl-1,2-ethanediyltitanium dichloride, (ethylamido)tetramethylcyclopentadienyl-1,2-ethanediyltitanium dichloride, (tert-butylamido)tetramethylcyclopentadienyl dimethylsilanetitanium dichloride, (benzylamido)tetramethylcyclopentadienyl dimethylsilanetitanium dichloride, (phenylphosphido)tetramethylcyclopentadienyl dimethylsilanetitanium dichloride, (tert-butylamido)indenyl-1,2-ethanediyltitanium dichloride, (tert-butylamido)tetrahydroindenyl-1,2-ethanediyl titanium dichloride, (tert-butylamido)fluorenyl-1,2-ethanediyltitanium dichloride, (tert-butylamido)indenyldimethylsilanetitanium dichloride, (tert-butylamido)tetrahydroindenyldimethylsilane titanium dichloride, (tert-butylamido)fluorenyldimethylsilanetitanium dichloride, (dimethylaminomethyl)tetramethylcyclopentadienyl titanium(III) dichloride, (dimethylaminoethyl)tetramethylcyclopentadienyl titanium(III) dichloride, (dimethylaminopropyl)tetramethylcyclopentadienyl-titanium (III) dichloride, (N-pyrrolidinylethyl)tetramethylcyclopentadienyl-titanium dichloride, (B-dimethylaminoborabenzene)cyclopentadienylzirconium dichloride, cyclopentadienyl(9-mesitylboraanthracenyl)zirconium dichloride, 2,2'-thiobis(4-methyl-6-tert-butylphenoxy)titanium dichloride, 2,2'-thiobis[4-methyl-6-(1-methylethyl) phenoxy]titanium dichloride, 2,2'-thiobis[4,6-dimethylphenoxy]titanium dichloride, 2,2'-methylenebis(4-methyl-6-tert-butylphenoxy)titanium dichloride, 2,2'-ethylenebis(4-methyl-6-tert-butylphenoxy)titanium dichloride, 2,2'-sulfinylbis(4-methyl-6-tert-butylphenoxy)titanium dichloride, 2,2'-(4,4',6,6'-tetra-tert-butyl-1,1'-biphenoxy)titanium dichloride, (di-tert-butyl-1,3-propanediamido)titanium dichloride, (dicyclohexyl-1,3-propanediamido)titanium dichloride, [bis(trimethylsilyl)-1,3-propanediamido] titanium dichloride, [bis(tert-butyldimethylsilyl)-1,3-propanediamido]titanium dichloride, [bis(2,6-dimethylphenyl)-1,3-propanediamido]titanium dichloride, [bis(2,6-diisopropylphenyl)-1,3-propanediamido]titanium dichloride, [bis(2,6-di-tert-butylphenyl)-1,3-propanediamidol]titanium dichloride, [bis(triisopropylsilyl)naphthalenediamido]titanium dichloride, [bis(trimethylsilyl)naphthalenediamido]titanium dichloride, [bis(tert-butyldimethylsilyl)naphthalenediamido]titanium dichloride, [bis(tert-butyldimethylsilyl)naphthalenediamido]titanium dibromide, cyclopentadienytitanium trichloride, pentamethylcyclopentadienyltitanium trichloride, [hydrotris(3,5-dimethylpyrazolyl)borate]titanium trichloride, [hydrotris(3,5-diethylpyrazolyl)borate]titanium trichloride, [hydrotris(3,5-di-tert-butylpyrazolyl)borate]titanium trichloride, [tris(3,5-dimethylpyrazolyl)methyl]titanium trichloride, [tris(3,5-diethylpyrazolyl)methyl]titanium trichloride and [tris(3,5-di-tert-butylpyrazolyl)methyl]titanium trichloride.

Still further examples of the metal compound represented by the formula [4], wherein M is a titanium atom, are compounds in which "dichloride" in the abnove-mentioned compounds is changed to "difluoride", "dibromide", "diiodide", "dimethyl", "diethyl", "diisopropyl", "diphenyl", "dibenzyl", "dimethoxide", "diethoxide", "di-n-propoxide", "diisopropoxide", "di-n-butoxide", "diisobutoxide", "di-tert-butoxide", "diphenoxide" or "di(2,6-di-tert-butylphenoxide", and compounds in which "trichloride" in the above-mentioned compounds is changed to "trifluoride", "tribromide", "triiodide", "trimethyl", "triethyl", "triisopropyl", "triphenyl", "tribenzyl", "trimethoxide", "triethoxide", "tri-n-propoxide", "triisopropoxide", "tri-n-butoxide", "triisobutoxide", "tri-tert-butoxide", "triphenoxide" or "tri(2,6-di-tert-butylphenoxide".

Examples of the metal compound represented by the formula [4], wherein M is a zirconium atom or a hafnium atom, are those in which a "titanium atom" in the above-mentioned compounds is changed to a "zirconium atom" or a "hafnium atom".

Examples of the metal compound represented by the formula [4], wherein M is a nickel atom, are 2,2'-methylenebis[(4R)-4-phenyl-5,5'-dimethyloxazoline]nickel dibromide, 2,2'-methylenebis[(4R)-4-phenyl-5,5'-diethyloxazoline]nickel dibromide, 2,2'-methylenebis[(4R)-4-phenyl-5,5'-di-n-propyloxazoline]nickel dibromide, 2,2'-methylenebis[(4R)-4-phenyl-5,5'-diisopropyloxazoline] nickel dibromide, 2,2'-methylenebis[(4R)-4-phenyl-5,5'-dicyclohexyloxazoline]nickel dibromide, 2,2'-methylenebis[(4R)-4-phenyl-5,5'-dimethosyoxazoline]nickel dibromide, 2,2'-methylenebis[(4R)-4-phenyl-5,5'-diethoxyoxazoline]

nickel dibromide, 2,2'-methylenebis[(4R)-4-phenyl-5,5'-diphenyloxazoline]nickel dibromide, methylenebis[(4R)-4-methyl-5,5'-di-(2-methylphenyl)oxazoline]nickel dibromide, methylenebis[(4R)-4-methyl-5,5'-di-(3-methylphenyl)oxazoline]nickel dibromide, methylenebis[(4R)-4-methyl-5,5'-di-(4-methylphenyl)oxazoline]nickel dibromide, methylenebis[(4R)-4-methyl-5,5'-di-(2-methoxyphenyl)oxazoline]nickel dibromide, methylenebis[(4R)-4-methyl-5,5'-di-(3-methoxyphenyl)oxazoline]nickel dibromide, methylenebis[(4R)-4-methyl-5,5'-di-(4-methoxyphenyl)oxazoline]nickel dibromide, methylenebis[spiro{(4R)-4-methyloxazoline-5,1'-cyclobutane}]nickel dibromide, methylenebis[spiro{(4R)-4-methyloxazoline-5,1'-cyclopentane}]nickel dibromide, methylenebis[spiro{(4R)-4-methyloxazoline-5,1'-cyclohexane}]nickel dibromide, methylenebis[spiro{(4R)-4-methyloxazoline-5,1'-cycloheptane}]nickel dibromide, 2,2'-methylenebis[(4R)-4-isopropyl-5,5-dimethyloxazoline]nickel dibromide, 2,2'-methylenebis[(4R)-4-isopropyl-5,5-diethyloxazoline]nickel dibromide, 2,2'-methylenebis[(4R)-4-isopropyl-5,5-di-n-propyloxazoline]nickel dibromide, methylenebis[(4R)-4-isopropyl-5,5-diisopropyloxazoline]nickel dibromide, 2,2'-methylenebis[(4R)-4-isopropyl-5,5-dicyclohexyloxazoline]nickel dibromide, 2,2'-methylenebis[(4R)-4-isopropyl-5,5-diphenyloxazoline]nickel dibromide, 2,2'-methylenebis[(4R)-4-isopropyl-5,5-di-(2-methylphenyl)oxazoline]nickel dibromide, 2,2'-methylenebis[(4R)-4-isopropyl-5,5-di-(3-methylphenyl)oxazoline]nickel dibromide, 2,2'-methylenebis[(4R)-4-isopropyl-5,5-di-(4-methylphenyl)oxazoline]nickel dibromide, 2,2'-methylenebis[(4R)-4-isopropyl-5,5-di-(2-methoxyphenyl)oxazoline]nickel dibromide, 2,2'-methylenebis[(4R)-4-isopropyl-5,5-di-(3-methoxyphenyl)oxazoline]nickel dibromide, 2,2'-methylenebis[(4R)-4-isopropyl-5,5-di-(4-methoxyphenyl)oxazoline]nickel dibromide, 2,2'-methylenebis[spiro{(4R)-4-isopropyloxazoline-5,1'-cyclobutane}]nickel dibromide, 2,2'-methylenebis[spiro{(4R)-4-isopropyloxazoline-5,1'-cyclopentane}]nickel dibromide, 2,2'-methylenebis[spiro{(4R)-4-isopropyloxazoline-5,1'-cyclohexane}]nickel dibromide, 2,2'-methylenebis[spiro{(4R)-4-isopropyloxazoline-5,1'-cycloheptane}]nickel dibromide, 2,2'-methylenebis[(4R)-4-isobutyl-5,5-dimethyloxazoline]nickel dibromide, 2,2'-methylenebis[(4R)-4-isobutyl-5,5-diethyloxazoline]nickel dibromide, 2,2'-methylenebis[(4R)-4-isobutyl-5,5-di-n-propyloxazoline]nickel dibromide, 2,2'-methylenebis[(4R)-4-isobutyl-5,5-diisopropyloxazoline]nickel dibromide, 2,2'-methylenebis[(4R)-4-isobutyl-5,5-dicyclohexyloxazoline]nickel dibromide, 2,2'-methylenebis[(4R)-4-isobutyl-5,5-diphenyloxazoline]nickel dibromide, 2,2'-methylenebis[(4R)-4-isobutyl-5,5-di-(2-methylphenyl)oxazoline]nickel dibromide, 2,2'-methylenebis[(4R)-4-isobutyl-5,5-di-(3-methylphenyl)oxazoline]nickel dibromide, 2,2'-methylenebis[(4R)-4-isobutyl-5,5-di-(4-methylphenyl)oxazoline]nickel dibromide, 2,2'-methylenebis[(4R)-4-isobutyl-5,5-di-(2-methoxyphenyl)oxazoline]nickel dibromide, 2,2'-methylenebis[(4R)-4-isobutyl-5,5-di-(3-methoxyphenyl)oxazoline]nickel dibromide, 2,2'-methylenebis[(4R)-4-isobutyl-5,5-di-(4-methoxyphenyl)oxazoline]nickel dibromide, 2,2'-methylenebis[spiro{(4R)-4-isobutyloxazoline-5,1'-cyclobutane}]nickel dibromide, 2,2'-methylenebis[spiro{(4R)-4-isobutyloxazoline-5,1'-cyclopentane}]nickel dibromide, 2,2'-methylenebis[spiro{(4R)-4-isobutyloxazoline-5,1'-cyclohexane}]nickel dibromide, 2,2'-methylenebis[spiro{(4R)-4-isobutyloxazoline-5,1'-cycloheptane}]nickel dibromide, 2,2'-methylenebis[(4R)-4-tert-butyl-5,5-dimethyloxaxoline]nickel dibromide, 2,2'-methylenebis[(4R)-4-tert-butyl-5,5-diethyloxazoline]nickel dibromide, 2,2'-methylenebis[(4R)-4-tert-butyl-5,5-di-n-propyloxazoline]nickel dibromide, 2,2'-methylenebis[(4R)-4-tert-butyl-5,5-diisopropyloxazoline]nickel dibromide, 2,2'-methylenebis[(4R)-4-tert-butyl-5,5-diphenyloxazoline]nickel dibromide, 2,2'-methylenebis[(4R)-4-tert-butyl-5,5-dicyclohexyloxazoline]nickel dibromide, 2,2'-methylenebis[(4R)-4-tert-butyl-5,5-di-(2-methylphenyl)oxazoline]nickel dibromide, 2,2'-methylenebis[(4R)-4-tert-butyl-5,5-di-(3-methylphenyl)oxazoline]nickel dibromide, 2,2'-methylenebis[(4R)-4-tert-butyl-5,5-di-(4-methylphenyl)oxazoline]nickel dibromide, 2,2'-methylenebis[(4R)-4-tert-butyl-5,5-di-(2-methoxyphenyl)oxazoline]nickel dibromide, 2,2'-methylenebis[(4R)-4-tert-butyl-5,5-di-(3-methoxyphenyl)oxazoline]nickel dibromide, 2,2'-methylenebis[(4R)-4-tert-butyl-5,5-di-(4-methoxyphenyl)oxazoline]nickel dibromide, 2,2'-methylenebis[spiro{(4R)-4-tert-butyloxazoline-5,1'-cyclobutane}]nickel dibromide, 2,2'-methylenebis[spiro{(4R)-4-tert-butyloxazoline-5,1'-cyclopentane}]nickel dibromide, 2,2'-methylenebis[spiro{(4R)-4-tert-butyloxazoline-5,1'-cyclohexane}]nickel dibromide, 2,2'-methylenebis[spiro{(4R)-4-tert-butyloxazoline-5,1'-cycloheptane}]nickel dibromide, 2,2'-methylenebis[(4R)-4-phenyl-5,5-dimethyloxazoline]nickel dibromide, 2,2'-methylenebis[(4R)-4-phenyl-5,5-diethyloxazoline]nickel dibromide, 2,2'-methylenebis[(4R)-4-phenyl-5,5-di-n-propyloxazoline]nickel dibromide, 2,2'-methylenebis[(4R)-4-phenyl-5,5-diisopropyloxazoline]nickel dibromide, 2,2'-methylenebis[(4R)-4-phenyl-5,5-dicyclohexyloxazoline]nickel dibromide, 2,2'-methylenebis[(4R)-4-phenyl-5,5-diphenyl]oxazoline]nickel dibromide, 2,2'-methylenebis[(4R)-4-phenyl-5,5-di-(2-methylphenyl)oxazoline]nickel dibromide, 2,2'-methylenebis[(4R)-4-phenyl-5,5-di-(3-methylphenyl)oxazoline]nickel dibromide, 2,2'-methylenebis[(4R)-4-phenyl-5,5-di-(4-methylphenyl)oxazoline]nickel dibromide, 2,2'-methylenebis[(4R)-4-phenyl-5,5-di-(2-methoxyphenyl)oxazoline]nickel dibromide, 2,2'-methylenebis[(4R)-4-phenyl-5,5-di-(3-methoxyphenyl)oxazoline]nickel dibromide, 2,2'-methylenebis[(4R)-4-phenyl-5,5-di-(4-methoxyphenyl)oxazoline]nickel dibromide, methylenebis[spiro{(4R)-4-phenyloxazoline-5,1'-cyclobutane}]nickel dibromide, 2,2'-methylenebis[spiro{(4R)-4-phenyloxazoline-5,1'-cyclopentane}]nickel dibromide, 2,2'-methylenebis[spiro{(4R)-4-phenyloxazoline-5,1'-cyclohexane}]nickel dibromide, 2,2'-methylenebis[spiro{(4R)-4-phenyloxazoline-5,1'-cycloheptane}]nickel dibromide, 2,2'-methylenebis[(4R)-4-benzyl-5,5-dimethyloxazoline]nickel dibromide, 2,2'-methylenebis[(4R)-4-benzyl-5,5-diethyloxazoline] nickel dibromide, 2,2'-methylenebis[(4R)-4-benzyl-5,5-di-n-propyloxazoline]nickel dibromide, 2,2'-methylenebis[(4R)-4-benzyl-5,5-diisopropyloxazoline]nickel dibromide, 2,2'-methylenebis[(4R)-4-benzyl-5,5-dicyclohexyloxazoline]nickel dibromide, 2,2'-methylenebis[(4R)-4-benzyl-5,5-diphenyl]oxazoline]nickel dibromide, 2,2'-methylenebis[(4R)-4-benzyl-5,5-di-(2-methylphenyl)oxazoline]nickel dibromide, 2,2'-methylenebis[(4R)-4-benzyl-5,5-di-(3-methylphenyl)oxazoline]nickel dibromide, 2,2'-methylenebis[(4R)-4-benzyl-5,5-di-(4-methylphenyl)oxazoline]nickel dibromide, 2,2'-methylenebis[(4R)-4-benzyl-5,5-di-(2-methoxyphenyl)oxazoline]nickel dibromide, 2,2'-methylenebis[(4R)-4-benzyl-5,5-di-(3-methoxyphenyl)oxazoline] nickel dibromide, 2,2'-methylenebis[(4R)-4-benzyl-5,5-di-(4-methoxyphenyl)oxazoline]nickel dibromide, 2,2'-methylenebis[spiro{(4R)-4-benzyloxazoline-5,1'-cyclobutane}]nickel dibromide, 2,2'-methylenebis[spiro{(4R)-4-benzyloxazoline-5,1'-cyclopentane}]nickel dibromide, 2,2'-methylenebis[spiro{(4R)-4-benzyloxazoline-5,1'-cyclohexane}]nickel dibromide, and 2,2'-methylenebis[spiro{(4R)-4-benzyloxazoline-5,1'-cycloheptane}] nickel dibromide; and antipodes and iastreomers of the above-mentioned compounds. Further examples thereof are [hydrotris(3,5-dimethylpyrazolyl)borate]nickel bromide, [hydrotris(3,5-diethylpyrazolyl)borate]nickel bromide, and [hydrotris(3,5-di-tert-butylpyrazolyl)borate]nickel bromide.

Still further examples of the metal compound represented by the formula [4], wherein M is a nickel atom, are compounds in which "dibromide" in the above-mentioned compounds is changed to "difluoride", "dichloride", "diiodide", "dimethyl", "diethyl", "diisopropyl", "diphenyl", "dibenzyl", "dimethoxide", "diethoxide", "di-n-propoxide", "diisopropoxide", "di-n-butoxide", "diisobutoxide", "di-tert-butoxide", "diphenoxide" or "di(2,6-di-tert-butylphenoxide)".

A further example of the metal compound represented by the formula [4], wherein M is a nickel atom, is a compound represented by the following formula [7]:

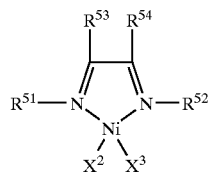

[7]

wherein each of $R^{51}$ and $R^{52}$ is a 2,6-diisopropylphenyl group; each of $R^{53}$ and $R^{54}$ is independently of each other a hydrogen atom or a methyl group, or $R^{53}$ and $R^{54}$ are combined to form an acenaphtene group; and each of $X^2$ and $X^3$ is independently of each other a fluorine atom, a chlorine atom, a bromine atom, an iodine atom, a methyl group, an ethyl group, a n-propyl group, an isopropyl group, a n-butyl group, a phenyl group, a benzyl group, a methoxy group, an ethoxy group, a n-propoxy group, an isopropoxy group, a n-butoxy group, an isobutoxy or a phenoxy group.

Further examples of the metal compound represented by the formula [4] are compounds in which a "nickel atom" in the above-mentioned nickel compounds is changed to a "palladium atom", a "cobalt atom", a "rhodium atom" or a "ruthenium atom".

Examples of the metal compound represented by the formula [4], wherein M is an iron atom, are 2,6-bis-[1-(2,6-dimethylphenylimino)ethyl]pyridineiron dichloride, 2,6-bis-[1-(2,6-diisopropylphenylimino)ethyl]pyridineiron dichloride, 2,6-bis-[1-(2-tert-butylphenylimino)ethyl]pyridineiron dichloride, [hydrotris(3,5-dimethylpyrazolyl)borate]iron chloride, [hydrotris(3,5-diethylpyrazolyl)borate] iron chloride, and [hydrotris(3,5-di-tert-butylpyrazolyl)borate]iron chloride; and compounds in which "dichloride" in the above-mentioned iron compounds is changed to "dibromide", "difluoride", "diiodide", "dimethyl", "diethyl", "diisopropyl", "diphenyl", "dibenzyl", "dimethoxide", "diethoxide", "di-n-propoxide", "diisopropoxide", "di-n-butoxide", "diisobutoxide", "di-tert-butoxide", "diphenoxide" or "di(2,6-di-tert-butylphenoxide)".

Further examples of the metal compound represented by the formula [4] are compounds obtained by changing an "iron atom" in the above-mentioned iron compounds to a "cobalt atom" or a "nickel atom".

Examples of the $\mu$-oxo type metal compound of the metal compound represented by the formula [4] are $\mu$-oxobis [isopropylidene(cyclopentadienyl)(2-phenoxy)titanium chloride], $\mu$-oxobis[isopropylidene(cyclopentadienyl)(3-tert-butyl-5-methyl-2-phenoxy)titanium chloride], $\mu$-oxobis [isopropylidene(methylcyclopentadienyl)(2-phenoxy)titanium chloride], $\mu$-oxobis[isopropylidene (methylcyclopentadienyl)(3-tert-butyl-5-methyl-2-phenoxy)titanium chloride], $\mu$-oxobis[isopropylidene (tetramethylcyclopentadienyl)(2-phenoxy)titanium chloride], $\mu$-oxobis[isopropylidene(tetramethylcyclopentadienyl)(3-tert-butyl-5methyl-2phenoxy)titanium methoxide], $\mu$-oxobis[dimethylsilylene(cyclopentadienyl)(2-phenoxy)titanium methoxide], $\mu$-oxobis[dimethylsilylene (cyclopentadienyl)(3-tert-butyl-5-methyl-2-phenoxy) titanium chloride], $\mu$-oxobis[dimethylsilylene (methylcyclopentadienyl)(2-phenoxy)titanium chloride], $\mu$-oxobis[dimethylsilylene(methylcyclopentadienyl)(3-tert-butyl-5-methyl-2-phenoxy)titanium chloride], $\mu$-oxobis [dimethylsilylene(tetramethylcyclopentadienyl)(2-phenoxy) titanium chloride], and $\mu$-oxobis[dimethylsilylene (tetramethylcyclopentadienyl)(3-tert-butyl-5-methyl-2-phenoxy)titanium chloride].

Further examples are compounds obtained by changing "chloride" in these compounds to "fluoride", "bromide", "iodide", "methyl", "ethyl", "isopropyl", "phenyl", "benzyl", "methoxide", "ethoxide", "n-propoxide", "isopropoxide", "n-butoxide", "isobutoxide", "tert-butoxide", "phenoxide" or "2,6-di-tert-butylphenoxide".

Further examples of the $\mu$-oxo type metal compound of the metal compound represented by the formula [4] are di-$\mu$-oxobis[isopropylidene(cyclopentadienyl)(2-phenoxy) titanium], di-$\mu$-oxobis[isopropylidene(cyclopentadienyl)(3-tert-butyl-5-methyl-2-phenoxy)titanium], di-$\mu$-oxobis[isopropylidene(methylcyclopentadienyl)(2-phenoxy)titanium], di-$\mu$-oxobis[isopropylidene(methylcyclopentadienyl)(3-tert-butyl-5-methyl-2-phenoxy)titanium], di-$\mu$-oxobis[isopropylidene(tetramethylcyclopentadienyl)(2-phenoxy)titanium], di-$\mu$-oxobis[isopropylidene(tetramethylcyclopentadienyl) (3-tert-butyl-5-methyl-2-phenoxy)titanium], di-$\mu$-oxobis [dimethylsilylene(cyclopentadienyl)(2-phenoxy)titanium], di-$\mu$-oxobis[dimethylsilylene(cyclopentadienyl)(3-tert-butyl-5-methyl-2-phenoxy)titanium], di-$\mu$-oxobis[dimethylsilylene(methylcyclopentadienyl)(2-phenoxy)titanium], di-$\mu$-oxobis[dimethylsilylene(methylcyclopentadienyl)(3-tert-butyl-5-methyl-2-phenoxy)titanium], di-$\mu$-oxobis [dimethylsilylene(tetramethylcyclopentadienyl)(2-phenoxy) titanium] and di-$\mu$-oxobis[dimethylsilylene (tetramethylcyclopentadienyl)(3-tert-butyl-5-methyl-2-phenoxy)titanium].

Other examples of the compound (B), wherein the metal atom is a nickel atom, are nickel chloride, nickel bromide, nickel iodide, nickel sulfate, nickel nitrate, nickel perchlorate, nickel acetate, nickel trifluoroacetate, nickel cyanide, nickel oxalate, nickel acetylacetonate, bis(allyl) nickel, bis (1,5-cyclooctadiene)nickel, dichloro(1,5-cyclooctadiene) nickel, dichlorobis(acetonitrile)nickel, dichlorobis(benzonitrile)nickel, carbonyl tris(triphenylphosphine)nickel, dichlorobis(triethylphosphine)nickel, di-acetobis(triphenylphosphine)nickel, tetrakis(triphenylphosphine)nickel, dichloro[1,2-bis(diphenylphosphino)ethane]nickel, bis[1,2-bis(diphenylphosphino)ethane]nickel, dichloro[1,3-bis (diphenylphosphino)propane]nickel, bis[1,3-bis(diphenylphosphino)propane]nickel, tetraamine nickel nitrate, tetrakis(acetonitrile)nickel tetrafluoroborate and nickel phthalocyanine.

Examples of the compound (B), wherein the metal atom is a vanadium atom, are vanadium acetylacetonate, vanadium tetrachloride and vanadium oxy trichloride. An example thereof, wherein the metal atom is a samarium atom, is bis(pentamethylcyclopentadienyl)samarium methyltetrahydrofuran. An example thereof, wherein the metal atom is an ytterbium atom, is bis(pentamethylcyclopentadienyl)ytterbium methyltetrahydrofuran.

The above-mentioned metal compounds as the compound (B) may be used singly, or may be used in combination of twe or more thereof.

The compound (B) is preferably a metal compound represented by the formula [4] more preferably a metal compound in which M in the formula [4] is the Group 4 atom in the periodic table, and further preferably a metal compound, which contains at least one group having a cyclopentadienyl type anion skeleton as $L^2$ in the formula [3].

As the organoaluminum compound (C) used for the catlyst for addition polymerization according to the present invention, known organoaluminum compounds can be used. Preferred is an organoaluminum compound represented by the following formula [8]:

   [8]

wherein d is a number satisfying $0<d\leq3$; $R^6$ is a hydrocarbon group, and when two or more $R^6$ groups exist, these may be the same or different; Y is a hydrogen atom, a halogen atom or an hydrocarbonoxy group, and when two or more Y's exist, they may be the same or different.

$R^6$ in the formula [8] is preferably a hydrocarbon group having 1 to 24 carbon atoms, and more preferably an alkyl group having 1 to 24 carbon atoms. Examples thereof are a methyl group, an ethyl group, a n-propyl group, a n-butyl group, an isobutyl group, a n-hexyl group, a 2-methylhexyl group and a n-octyl group. More preferred is an ethyl group, a n-butyl group, an isobutyl group, a n-hexyl group or a n-octyl group.

Examples of the halogen arom as Y in the formula [8] are a fluorine atom, a chlorine atom, a bromine atom and an iodine atom, and preferred is a chlorine atom.

The hydrocarbonoxy group as Y in the formula [8] is preferably an alkoxy group, an aralkyloxy group or an aryloxy group.

Examples of the alkoxy group as Y in the formula [8] are a methoxy group, an ethoxy group, a n-propoxy group, an isopropoxy group, a n-butoxy group, a sec-butoxy group, a tert-butoxy group, a n-pentoxy group, a neopentoxy group, a n-hexoxy group, a n-octoxy group, a n-dodecoxy group, a n-pentadecoxy group and a n-eicosoxy group.

The alkoxy group as Y in the formula [8] is preferably an alkoxy group having 1 to 24 carbon atoms, and more preferably a methoxy group, an ethoxy group or a tert-butoxy group.

Examples of the aryloxy group as Y in the formula [8] are a phenoxy group, a 2-methylphenoxy group, a 3-methylphenoxy group, a 4-methylphenoxy group, a 2,3-dimethylphenoxy group, a 2,4-dimethylphenoxy group, a 2,5-dimethylphenoxy group, a 2,6-dimethylphenoxy group, a 3,4-dimethylphenoxy group, a 3,5-dimethylphenoxy group, a 2,3,4-trimethylphenoxy group, a 2,3,5-trimethylphenoxy group, a 2,3,6-trimethylphenoxy group, a 2,4,5-trimethylphenoxy group, a 2,4,6-trimethylphenoxy group, a 3,4,5-trimethylphenoxy group, a 2,3,4,5-tetramethylphenoxy group, a 2,3,4,6-tetramethylphenoxy group, 2,3,5,6-tetramethylphenoxy group, a pentamethylphenoxy group, an ethylphenoxy group, a n-propylphenoxy group, an isopropylphenoxy group, a n-butylphenoxy group, a sec-butylphenoxy group, a tert-butylphenoxy group, a n-hexylphenoxygroup, a n-octylphenoxygroup, a n-decylphenoxy group, a n-tetradecylphenoxy group, a naphthoxy group and an anthrathenoxy group.

The aryloxy group as Y in the formula [8] is preferably an aryloxy group having 6 to 24 carbon atoms.

Examples of the aralkyloxy group as Y in the formula [8] are a benzyloxy group, a (2-methylphenyl)methoxy group, a (3-methylphenyl)methoxy group, a (4-methylphenyl)methoxy group, a (2,3-dimethylphenyl)methoxy group, a (2,4-dimethylphenyl)methoxy group, a (2,5-dimethylphenyl)methoxy group, a (2,6-dimethylphenyl)methoxy group, a (3,4-dimethylphenyl)methoxy group, a (3,5-dimethylphenyl)methoxy group, a (2,3,4-trimethylphenyl)methoxy group, a (2,3,5-trimethylphenyl)methoxy group, a (2,3,6-trimethylphenyl)methoxy group, a (2,4,5-trimethylphenyl)methoxy group, a (2,4,6-trimethylphenyl)methoxy group, a (3,4,5-trimethylphenyl)methoxy group, a (2,3,4,5-tetramethylphenyl)methoxy group, a (2,3,4,6-tetramethylphenyl)methoxy group, a (2,3,5,6-tetramethylphenyl)methoxy group, a (pentamethylphenyl)methoxy group, an (ethylphenyl)methoxy group, a (n-propylphenyl)methoxy group, an (isopropylphenyl)methoxy group, a (n-butylphenyl)methoxy group, a (sec-butylphenyl)methoxy group, a (tert-butylphenyl)methoxy group, a (n-hexylphenyl)methoxy group, a (n-octylphenyl)methoxy group, a (n-decylphenyl)methoxy group, a (n-tetradecylphenyl)methoxy group, a naphthylmethoxy group and an anthrathenylmethoxy group.

The aralkyloxy group as Y in the formula [8] is preferably an aralkyloxy group having 7 to 24 carbon atoms, and more preferably a benzyloxy group.

These alkoxy, aryloxy and aralkyloxy groups abovementioned as Y may be respectively substituted with a halogen atom such as a fluorine atom, a chlorine atom, a bromine atom and an iodine atom; an alkoxy group such as a methoxy group and an ethoxy group; or an aryloxy group such as a phenoxy group.

Examples of the organoaluminum compound represented by the formula [8] are a trialkylaluminum such as trimethylaluminum, triethylaluminum, tri-n-propylaluminum, tri-n-butylaluminum, triisobutylaluminum, tri-n-hexylaluminum and tri-n-octylaluminum; a dialkylaluminum chloride such as dimethylaluminum chloride, diethylaluminum chloride, di-n-propylaluminum chloride, di-n-butylaluminum chloride, diisobutylaluminum chloride and di-n-hexylaluminum chloride; an alkylaluminum dichloride such as methylaluminum dichloride, ethylaluminum dichloride, n-propylaluminum dichloride, n-butylaluminum dichloride, isobutylaluminum dichloride and n-hexylaluminum dichloride; a dialkylaluminum hydride such as dimethylaluminum hydride, diethylaluminum hydride, di-n-propylaluminum hydride, di-n-butylaluminum hydride, diisobutylaluminum hydride and di-n-hexylaluminum hydride; an alkyl(dialkoxy)aluminum such as methyl(dimethoxy)aluminum, methyl(diethoxy)aluminum and methyl(di-tert-butoxy)aluminum; a dialkyl(alkoxy)aluminum such as dimethyl(methoxy)aluminum, dimethyl(ethoxy)aluminum and dimethyl(tert-butoxy)aluminum; an alkyl(diaryloxy)aluminum such as methyl(diphenoxy)aluminum, methylbis(2,6-diisopropylphenoxy)aluminum and methylbis(2,6-diphenylphenoxy) aluminum; and a dialkyl(aryloxy)aluminum such as dimethyl(phenoxy)aluminum, dimethyl(2,6-diisopropylphenoxy) aluminum and dimethyl(2,6-diphenylphenoxy)aluminum.

Among them, preferred is a trialkylaluminum, further preferred is trimethylaluminum, triethylaluminum, tri-n-butylaluminum, triisobutylaluminum or tri-n-hexylaluminum, and particularly preferred is triisobutylaluminum or tri-n-hexylaluminum.

These organoaluminum compounds may be used alone, or in combination of two or more thereof.

The ratio (molar ratio) of the amount of the respective catalyst components used in the present invention is not particularly limited. The molar ratio of the component (A) to the component (B) is usually in a range of (A):(B)=from 1:1 to 10000:1, preferably from 1:1 to 5000:1, and further preferably from 1:1 to 1000:1. The amount of the component (C) is usually in a range of (B):(C)=from 0.1:1 to 1:10000, and preferably from 1:1 to 1:1000.

As the catalyst for addition polymerization of the present invention, a reaction product obtained by preliminarily contacting the component (A) and the component (B), optionally, further the component (C) may be also used, and they may be also used by being separately charged in a polymerization vessel. The arbitrary two components among them may be also previously contacted, and further, another component may be also contacted.

Examples of the addition polymerizable monomer in the present invention are an olefin, a diolefin, a cyclic olefin, an alkenyl aromatic hydrocarbon and a polar monomer, each of which has 2 to 100 carbon atoms. A combination of two or more thereof may be used.

Examples thereof are an olefin such as ethylene, propylene, 1-butene, 1-pentene, 4-methyl-1-pentene-1,5-methyl-1-hexene, 1-hexene, 1-heptene, 1-octene, 1-nonene, 1-decene and vinylcyclohexane; a diolefin such as 1,5-hexadiene, 1,4-hexadiene, 1,4-pentadiene, 1,7-octadiene, 1,8-nonadiene, 1,9-decadiene, 4-methyl-1,4-hexadiene, 5-methyl-1,4-hexadiene, 7-methyl-1,6-octadiene, 5-ethylidene-2-norbornene, dicyclopentadiene, 5-vinyl-2-norbornene, 5-methyl-2-norbornene, norbornadiene, 5-methylene-2-norbornene, 1,5-cyclooctadiene, 5,8-endomethylenehexahydronaphthalene, 1,3-butadiene, isoprene, 1,3-hexadiene, 1,3-octadiene, 1,3-cyclooctadiene and 1,3-cyclohexadiene; a cyclic olefin such as norbornene, 5-methylnorbornene, 5-ethylnorbornene, 5-butylnorbornene, 5-phenylnorbornene, 5-benzylnorbornene, tetracyclododecene, tricyclodecene, tricycloundecene, pentacyclopentadecene, pentacyclohexadecene, 8-methyltetracyclododecene, 8-ethyltetracyclododecene, 5-acetylnorbornene, 5-acetyloxynorbornene, 5-methoxycarbonylnorbornene, 5-ethoxycarbonylnorbornene, 5-methyl-5-methoxycarbonylnorbornene, 5-cyanonorbornene, 8-methoxycarbonyltetracyclododecene, 8-methyl-8-tetracyclododecene and 8-cyanotetracyclododecene; an alkenyl aromatic hydrocarbon such as an alkenylbenzene (e.g. styrene, 2-phenylpropylene, 2-phenylbutene and 3-phenylpropylene), an alkylstyrene (e.g. p-methylstyrene, m-methylstyrene, o-methylstyrene, p-ethylstyrene, m-ethylstyrene, o-ethylstyrene, 2,4-dimethylstyrene, 2,5-dimethylstyrene, 3,4-dimethylstyrene, 3,5-dimethylstyrene, 3-methyl-5-ethylstyrene, p-tert-butylstyrene and p-sec-butylstyrene), a bis (alkenyl)benzene (e.g. divinylbenzene) and an alkenylnaphthalene (e.g. 1-vinylnaphthalene); and a polar monomer such as an α, β-unsaturated carboxylic acid (e.g. acrylic acid, methacrylic acid, fumaric acid, maleic anhydride, itaconic acid, itaconic anhydride and bicyclo(2,2,1)-5-heptene-2,3-dicarboxylic acid), and metal salts thereof (e.g. salts of sodium, potassium, lithium, zinc, magnesium and calcium), an α, β-unsaturated carboxylic acid ester (e.g. methyl acrylate, ethyl acrylate, n-propyl acrylate, isopropyl acrylate, tert-butyl acrylate, 2-ethylhexyl acrylate, methyl methacrylate, ethyl methacrylate, n-propyl methacrylate, isopropyl methacrylate, n-butyl methacrylate and isobutyl methacrylate), an unsaturated dicarboxylic acid (e.g. maleic acid and itaconic acid ), a vinyl ester (e.g. vinyl acetate, vinyl propionate, vinyl capronate, vinyl caprate, vinyl laurate, vinyl stearate and vinyl trifluoroacetate), an unsaturated carboxylic acid glycidylate (e.g. acrylic acid glycidylate, methacrylic acid glycidylate and itaconic acid monoglycidylate), and a cyclic ether (e.g. ethylene oxide, propylene oxide, 1-hexene oxide, cyclohexene oxide, styrene oxide and tetrahydrofuran).

The catalyst for addition polymerization of the present invention can be applied to homopolymerzation or copolymerzation of these monomers. Examples of a combination of monomers constituting the copolymer are ethylene and propylene; ethylene and 1-butene; ethylene and 1-hexene; and propylene and 1-butene.

The catalyst for olefin polymerization according to the present invention is particularly preferable as a catalyst for olefin polymerization, and is preferably used for a process for producing an olefin polymer. The olefin polymer is particularly preferably copolymers of ethylene with an α-olefin. Among them, preferred is a copolymer of ethylene with an α-olefin having a polyethylene crystal structure. The α-olefin has preferably 3 to 8 carbon atoms, and examples thereof are 1-butene, 1-hexene and 1-octene.

A polymerization method is not particularly limited. For example, there can be exemplified a solvent polymerization method and a slurry polymerization method, in which an aliphatic hydrocarbon (e.g. butane, pentane, hexane, heptaneandoctane), an aromatic hydrocarbon (e.g. benzene and toluene) or a halogenated hydrocarbon (e.g. methylene dichloride) is used as a solvent; a bulk polymerization method, in which polymerization is carried out in a liquid monomer; a gas phase polymerization method, in which polymerization is carried out in a gaseous monomer; and a high-pressure polymerization method, in which polymerization is carried out in a supercritical liquid condition at a high temperature under a high pressure. As a polymerization type, either of a batch-wise type and a continuous type is possible.

A method of feeding the respective components in a reactor is not particularly limited. Examples thereof are a method of feeding them in a solid condition; and a method of feeding them in a condition of a solution, a suspension or a slurry, using a hydrocarbon solvent, from which components deactivating catalyst components such as moisture and oxygen are completely removed, When the respective components are used as a solution, the concentration of the component (A) and the component (C) are usually from 0.0001 to 100 mmol/L, and preferably from 0.01 to 10 mmol/L, converted to a metal atom, respectively. The concentration of the component (B) is usually from 0.0001 to 100 mmol/L, and preferably from 0.01 to 10 mmol/L, converted to a metal atom.

The polymerization temperature is usually from −100 to 350° C., preferably from −20 to 300° C., and more preferably from 20 to 300° C. The polymerization pressure is usually from 0.1 to 350 MPa, preferably from 0.1 to 300 MPa, and more preferably from 0.1 to 200 MPa. In general, the polymerization time can be appropriately determined according to the kind of a desired polymer and a reaction apparatus, and a range of from 1 minute to 20 hours can be adopted.

In order to control a molecular weight of an addition polymer, a chain transfer agent such as hydrogen may be added.

EXAMPLES

The present invention is further illustrated in detail according to Examples and Comparative Examples below, but the present invention is not limited thereto.

The measurement values of respective items in Examples were measured according to methods described below.

(1) Content of α-Olefin Unit in Copolymer (Short Chain Branch Degree: SCB)

The content of an α-olefin unit in an obtained polymer was determined from an IR absorption spectrum, wherein the measurement and calculation were carried out by using characteristic absorptions derived from the α-olefin, according to a method described in "Die Makromoleculare Chemie, 177, 449 (1976) McRae, M. A., Madams, W. F.", and the IR absorption spectrum was obtained by a measurerent using an infrared spectrometer (FT-IR7300, manufactured by NIPPON BUNKO Inc.).

(2) Intrinsic Viscosity ([η])

It was measured at 135° C. in a tetralin solution using an Ubbelohde viscometer.

(3) Molecular Weight and Molecular Weight Distribution

They were determined under the under-mentioned conditions according to a gel permeation chromatography (GPC). A calibration curve was prepared using standard polystyrenes. Molecular weight distribution was evaluated by a ratio, (Mw/Mn), of a weight average molecular weight (Mw) to a number average molecular weight (Mn):

equipment: 150C. type, manufactured by Milipore Waters Co., Ltd.,
    column: TSK-GEL GMH-HT, 7.5×600×2 columns,
    measurement temperature: 140° C.,
    solvent: o-dichlorobenzene, and
    measurement concentration: 5 mg/5 ml.

Example 1

(1) Preparation of Bismuth Compound

Into a 300 ml four-necked flask purged with argon, 9.88 g (22.4 mmol) of triphenyl bismuth and 100 ml of toluene were charged, and the mixture was stirred at room temperature. Thereto, a solution of 12.6 g (68.5 mmol) of pentafluorophenol in 100 ml of toluene was added dropwise. Thereafter, the mixture was stirred for 15.5 hours at room temperature. Then, the reaction was carried out (i) for 4 hours under a toluene-refluxing condition, (ii) for 18 hour at room temperature, (iii) for 7 hours under a toluene-refluxing condition, and (iv) for 17 hour at room temperature. A formed yellow needle-like crystal was filtered, and dried under vacuum at room temperature, thereby obtaining 12.6 g of a yellow crystal.

Next, into a 100 ml four-necked flask purged with argon, 0.978 g (1.15 mmol) of said yellow crystal and 30 ml of toluene were charged. Thereto, 0.250 g (1.18 mmol) of pentafluorophenylboric acid and 10 ml of toluene were charged at room temperature. The mixture was stirred for 3 hours under a refluxing condition. By allowing the mixture to stand without stirring, a white precipitation was formed, and the supernatant liquid was a yellow clear liquid. A white crystal was obtained by distilling out volatile components under vacuum, and drying.

(2) Production of Addition Polymer

After drying under vacuum an autoclave reactor having an inner volume of 400 ml equipped with a stirrer, and replacing the atmosphere thereof with argon, 190 ml of hexane as a solvent and 10 ml of 1-hexene as a comonomer were charged, and the reactor was heated to 70° C. Then, ethylene was fed while adjusting at an ethylene pressure of 0.6 MPa. After the system was stabilized, 0.25 ml (250 μmol) of triisobutylaluminum (1 mmol/ml, toluene solution) was charged, successively, 0.5 ml (1 μmol) of ethylenebis(indenyl)ziconium dichloride (2 μmol/ml, toluene solution) was charged, and then, 73.9 mg of the white crystal obtained in the above (1) was charged. The polymerization was carried out at 70° C. for 30 minutes under feeding ethylene to keep the constant total pressure. As a result, 1.97 g of an ethylene-1-hxene copolymer was obtained. The polymerization activity, SCB, Mw and Mw/Mn were 3.9×10$^6$ g/mol-Zr/hour, 16.4, 66000 and 2.1, respectively.

Comparative Example 1

Example 1 was repeated except that 73.9 mg of the white crystal used in Example 1 (2) was changed to 49.8 mg (113 μmol) of tripheny bismuth. As a result, only a trace of an ethylene-1-hxene copolymer was obtained.

Comparative Example 2

Example 1 was-repeated except that 73.9 mg of the white crystal used in Example 1 (2) was changed to 60.9 mg (71.6 μmol) of the yellow crystal prepared in Example 1 (1). As a result, only a trace of an ethylene-1-hxene copolymer was obtained.

Comparative Example 3

(1) Preparation of Bismuth Compound

Into a 100 ml four-necked flask purged with argon, 0.957 g (1.13 mmol) of the yellow crystal prepeared in Example 1 (1) and 30 ml of toluene were charged. Thereto, 0.120 g (0.568 mmol) of pentafluorophenylboronic acid and 10 ml of toluene were charged at room temperature. The mixture was stirred for three hours under a refluxing condition to obtain a toluene solution of the bismuth compound, which solution had a concentration of the bismuth compound of 28.2 μmol-Bi/ml, which concentration was calculated from the charged amounts of the compounds.

(2) Production of Addition Polymer

Example 1 (2) was repeated except that 73.9 mg of the white crystal used therein was changed to 5 ml of the solution obtained in the above (1). As a result, only a trace of an ethylene-1-hxene copolymer was obtained.

The invention claimed is:

1. A process for producing a metal compound, which comprises the step of contacting with one other the following component (a), 0.1 to 8 mol of the following component (b) per 1 mol of the component (a), and 0.6 to 8 mol of the following component (c) per 1 mol of the component (a):

(a) a compound represented by the following formula [1], $$BiL^1_r \qquad [1],$$

(b) a compound represented by the following formula [2], $$R^1_{s-1}TH \qquad [2], \text{ and}$$

(c) a compound represented by the following formula [3], $$R^2_{3-n}J(OH)_n \qquad [3],$$

wherein r is the valence of Bi; $L^1$ is a hydrogen atom, a halogen atom, a hydrocarbon group or a hydrocarbonoxy group, and when two or more $L^1$'s exist, they are the same as or different from one another; T is a non-metal atom of the Group 15 or 16 in the periodic table; s is the valence of T; $R^1$ is an electron-withdrawing group or an electron-withdrawing group-containing group, and when two or more $R^1$'s exist, they are the same as or different from one another; n is 2 or 3; J is an atom of the Group 13 in the periodic table; and $R^2$ is a hydrocarbon group, and when two or more $R^2$'s exist, they are the same as or different from one another.

2. The process for producing a metal compound according to claim 1, wherein T is a nitrogen atom or an oxygen atom.

3. The process for producing a metal compound according to claim 1, wherein $R^1$ is a halogenated hydrocarbon group.

4. The process for producing a metal compound according to claim 1, wherein the component (b) is a fluorinated phenol.

5. The process for producing a metal compound according to claim 1, wherein the component (b) is pentafluorophenol.

6. The process for producing a metal compound according to claim 1, wherein Bi has the valence of 3.

7. The process for producing a metal compound according to claim 1, wherein J is a boron atom.

* * * * *